United States Patent
Weber et al.

(10) Patent No.: US 9,873,714 B2
(45) Date of Patent: *Jan. 23, 2018

(54) PROCESSES FOR PREPARING OF GLUCOPYRANOSYL-SUBSTITUTED BENZYL-BENZENE DERIVATIVES

(71) Applicant: Boehringer Ingelheim International GmbH, Ingelheim am Rhein (DE)

(72) Inventors: Dirk Weber, Mainz (DE); Tobias Fiedler, Ockenheim (DE); Christian Filser, Ladenburg (DE); Rainer Hamm, Ingelheim am Rhein (DE); Simone Orlich, Schoeneberg (DE); Matthias Post, Eltville-Martinsthal (DE); Svenja Renner, Eckenroth (DE); Xiao-Jun Wang, Danbury, CT (US); Thomas Wirth, Stadecken-Elsheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/680,318

(22) Filed: Apr. 7, 2015

(65) Prior Publication Data
US 2015/0218200 A1 Aug. 6, 2015

Related U.S. Application Data

(63) Continuation of application No. 12/892,326, filed on Sep. 28, 2010, now Pat. No. 9,024,010.

(60) Provisional application No. 61/247,144, filed on Sep. 30, 2009.

(51) Int. Cl.
*C07H 15/26* (2006.01)
*C07H 1/00* (2006.01)
*C07D 309/10* (2006.01)

(52) U.S. Cl.
CPC ........ *C07H 15/26* (2013.01); *C07D 309/10* (2013.01); *C07H 1/00* (2013.01)

(58) Field of Classification Search
None
See application file for complete search history.

(56) References Cited

U.S. PATENT DOCUMENTS

| | | |
|---|---|---|
| 3,174,901 A | 3/1965 | Sterne |
| 3,884,906 A | 5/1975 | Van Der Meer et al. |
| 4,379,785 A | 4/1983 | Weyer et al. |
| 4,602,023 A | 7/1986 | Kiely et al. |
| 4,639,436 A | 1/1987 | Junge et al. |
| 4,786,023 A | 11/1988 | Harris et al. |
| 4,786,755 A | 11/1988 | Kiely et al. |
| 5,880,289 A | 3/1999 | Kaneko et al. |
| 6,414,126 B1 | 7/2002 | Ellsworth et al. |
| 6,498,193 B2 | 12/2002 | Beisswenger et al. |
| 6,515,117 B2 | 2/2003 | Ellsworth et al. |
| 6,613,806 B1 | 9/2003 | Aven et al. |
| 6,627,611 B2 | 9/2003 | Tomiyama et al. |
| 6,774,112 B2 | 8/2004 | Gougoutas |
| 6,794,480 B2 | 9/2004 | Goto et al. |
| 6,936,590 B2 | 8/2005 | Washburn et al. |
| 6,972,283 B2 | 12/2005 | Fujikura et al. |
| 7,101,856 B2 | 9/2006 | Glombik et al. |
| 7,169,761 B2 | 1/2007 | Tomiyama et al. |
| 7,202,350 B2 | 4/2007 | Imamura et al. |
| 7,371,732 B2 | 5/2008 | Eickelmann et al. |
| 7,375,087 B2 | 5/2008 | Teranishi et al. |
| 7,375,090 B2 | 5/2008 | Himmelsbach et al. |
| 7,375,213 B2 | 5/2008 | Deshpande et al. |
| 7,393,836 B2 | 7/2008 | Eckhardt et al. |
| 7,407,955 B2 | 8/2008 | Himmelsbach et al. |
| 7,417,032 B2 | 8/2008 | Eckhardt et al. |
| 7,419,959 B2 | 9/2008 | Eckhardt et al. |
| 7,541,341 B2 | 6/2009 | Fushimi et al. |
| 7,579,449 B2 | 8/2009 | Eckhardt et al. |
| 7,589,193 B2 | 9/2009 | Washburn et al. |

(Continued)

FOREIGN PATENT DOCUMENTS

| | | |
|---|---|---|
| CA | 2382480 A1 | 3/2001 |
| CA | 2388818 A1 | 4/2001 |

(Continued)

OTHER PUBLICATIONS

Silverman, Handbook of Grignard Reagents, Marcel Dekker 1996, p. 82.*
McHale, Grignard Reaction, Connexions module: m15245, Oct. 14, 2007.*
Krasovskiy, Angew. Chem. Int. Ed. 2004, 43, 3333-3336.*
Lab Cat, Strong and Weak Acids, internet article, https://cdavies.wordpress.com/2007/02/27/strong-and-weak-acids/, Feb. 2007.*
Mooradian, Arsharg D. et al. "Narrative Review: A Rational Approach to Starting Insulin Therapy" (2006) Annals of Internal Medicine, vol. 145, pp. 125-134.

(Continued)

*Primary Examiner* — Layla D Berry
(74) *Attorney, Agent, or Firm* — Marc A. Began; Edouard G. Lebel

(57) ABSTRACT

The present invention relates to processes for preparing a glucopyranosyl-substituted benzyl-benzene derivative of general formula III,

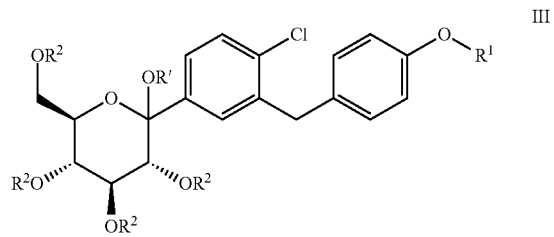

wherein $R^1$ is defined according to claim 1.

19 Claims, No Drawings

(56) References Cited

U.S. PATENT DOCUMENTS

| | | |
|---|---|---|
| 7,662,790 B2 | 2/2010 | Himmelsbach et al. |
| 7,674,486 B2 | 3/2010 | Bhaskaran et al. |
| 7,683,160 B2 | 3/2010 | Eckhardt et al. |
| 7,687,469 B2 | 3/2010 | Eckhardt et al. |
| 7,713,938 B2 | 5/2010 | Himmelsbach et al. |
| 7,723,309 B2 | 5/2010 | Himmelsbach et al. |
| 7,723,379 B2 | 5/2010 | Romanczyk, Jr. et al. |
| 7,745,414 B2 | 6/2010 | Eckhardt et al. |
| 7,772,191 B2 * | 8/2010 | Eckhardt ............. C07H 15/203 514/23 |
| 7,772,192 B2 | 8/2010 | Esko |
| 7,772,378 B2 | 8/2010 | Himmelsbach et al. |
| 7,772,407 B2 | 8/2010 | Imamura et al. |
| 7,776,830 B2 | 8/2010 | Eckhardt et al. |
| 7,847,074 B2 | 12/2010 | Eckhardt et al. |
| 7,851,502 B2 | 12/2010 | Bindra et al. |
| 7,851,602 B2 | 12/2010 | Himmelsbach et al. |
| 7,858,587 B2 | 12/2010 | Eckhardt et al. |
| 7,879,806 B2 | 2/2011 | Himmelsbach et al. |
| 7,879,807 B2 | 2/2011 | Himmelsbach et al. |
| 8,039,441 B2 | 10/2011 | Himmelsbach et al. |
| 8,119,648 B2 | 2/2012 | Himmelsbach et al. |
| 8,178,541 B2 | 5/2012 | Himmelsbach et al. |
| 8,232,281 B2 | 7/2012 | Dugi et al. |
| 8,283,326 B2 | 10/2012 | Eckhardt et al. |
| 8,507,450 B2 | 8/2013 | Eckhardt et al. |
| 8,551,957 B2 | 10/2013 | Dugi et al. |
| 8,557,782 B2 | 10/2013 | Eckhardt et al. |
| 8,802,842 B2 | 8/2014 | Weber et al. |
| 9,024,010 B2 | 5/2015 | Weber et al. |
| 9,034,883 B2 | 5/2015 | Klein et al. |
| 9,127,034 B2 | 9/2015 | Eckhardt et al. |
| 9,192,616 B2 | 11/2015 | Johnson |
| 2002/0137903 A1 | 9/2002 | Ellsworth et al. |
| 2003/0064935 A1 | 4/2003 | Gougoutas |
| 2003/0087843 A1 | 5/2003 | Washburn |
| 2003/0114390 A1 | 6/2003 | Washburn et al. |
| 2003/0212070 A1 | 11/2003 | Schwink et al. |
| 2004/0138148 A1 | 7/2004 | Fushimi et al. |
| 2004/0138439 A1 | 7/2004 | Deshpande et al. |
| 2005/0065098 A1 | 3/2005 | Fujikura et al. |
| 2005/0085680 A1 * | 4/2005 | Auerbach ............... B09B 3/00 588/315 |
| 2005/0124555 A1 | 6/2005 | Tomiyama et al. |
| 2005/0187168 A1 | 8/2005 | Eickelmann et al. |
| 2005/0209166 A1 | 9/2005 | Eckhardt et al. |
| 2005/0233982 A1 | 10/2005 | Himmelsbach et al. |
| 2006/0009400 A1 | 1/2006 | Eckhardt et al. |
| 2006/0019948 A1 | 1/2006 | Eckhardt et al. |
| 2006/0025349 A1 | 2/2006 | Eckhardt et al. |
| 2006/0035841 A1 | 2/2006 | Eckhardt et al. |
| 2006/0063722 A1 | 3/2006 | Washburn et al. |
| 2006/0074031 A1 | 4/2006 | Eckhardt et al. |
| 2006/0142210 A1 | 6/2006 | Eckhardt et al. |
| 2006/0189548 A1 | 8/2006 | Himmelsbach et al. |
| 2006/0210627 A1 | 9/2006 | Pfeffer et al. |
| 2006/0234953 A1 | 10/2006 | Himmelsbach et al. |
| 2006/0251728 A1 | 11/2006 | Himmelsbach et al. |
| 2006/0258749 A1 | 11/2006 | Eckhardt et al. |
| 2007/0004648 A1 | 1/2007 | Himmelsbach et al. |
| 2007/0027092 A1 | 2/2007 | Himmelsbach et al. |
| 2007/0042042 A1 | 2/2007 | Jo et al. |
| 2007/0049537 A1 | 3/2007 | Eckhardt et al. |
| 2007/0054867 A1 | 3/2007 | Eckhardt et al. |
| 2007/0073046 A1 | 3/2007 | Eckhardt et al. |
| 2007/0249544 A1 | 10/2007 | Himmelsbach et al. |
| 2007/0259821 A1 | 11/2007 | Eckhardt et al. |
| 2007/0281940 A1 | 12/2007 | Dugi et al. |
| 2008/0058379 A1 | 3/2008 | Eckhardt et al. |
| 2008/0107731 A1 | 5/2008 | Kohlrausch et al. |
| 2008/0234367 A1 | 9/2008 | Washburn et al. |
| 2008/0287529 A1 | 11/2008 | Deshpande et al. |
| 2009/0023913 A1 | 1/2009 | Eckhardt et al. |
| 2009/0137499 A1 | 5/2009 | Honda et al. |
| 2009/0281078 A1 | 11/2009 | Routledge et al. |
| 2009/0318547 A1 | 12/2009 | Eckhardt et al. |
| 2009/0326215 A1 | 12/2009 | Eckhardt et al. |
| 2010/0069310 A1 | 3/2010 | Himmelsbach et al. |
| 2010/0074950 A1 | 3/2010 | Sesha |
| 2010/0081625 A1 | 4/2010 | Wienrich et al. |
| 2010/0093654 A1 | 4/2010 | Himmelsbach et al. |
| 2010/0099641 A1 | 4/2010 | Himmelsbach et al. |
| 2010/0179191 A1 | 7/2010 | Himmelsbach et al. |
| 2010/0209506 A1 | 8/2010 | Eisenreich |
| 2010/0240879 A1 | 9/2010 | Eckhardt et al. |
| 2010/0249392 A1 | 9/2010 | Eckhardt et al. |
| 2010/0298243 A1 | 11/2010 | Manuchehri et al. |
| 2010/0317847 A1 | 12/2010 | Eckhardt et al. |
| 2011/0014284 A1 | 1/2011 | Eisenreich et al. |
| 2011/0015225 A1 | 1/2011 | Murata et al. |
| 2011/0046076 A1 | 2/2011 | Eickelmann et al. |
| 2011/0046087 A1 | 2/2011 | Eickelmann et al. |
| 2011/0065731 A1 | 3/2011 | Dugi et al. |
| 2011/0077212 A1 | 3/2011 | Seed et al. |
| 2011/0098240 A1 | 4/2011 | Dugi et al. |
| 2011/0178033 A1 | 7/2011 | Eckhardt et al. |
| 2011/0195917 A1 | 8/2011 | Dugi et al. |
| 2011/0206766 A1 | 8/2011 | Friedl et al. |
| 2011/0236477 A1 | 9/2011 | Schneider et al. |
| 2011/0237526 A1 | 9/2011 | Weber et al. |
| 2011/0237789 A1 | 9/2011 | Weber et al. |
| 2012/0041069 A1 | 2/2012 | Sesha |
| 2012/0071403 A1 | 3/2012 | Strumph et al. |
| 2012/0094894 A1 | 4/2012 | Graefe-Mody et al. |
| 2012/0196812 A1 | 8/2012 | Eickelmann et al. |
| 2012/0219622 A1 | 8/2012 | Kohlrausch et al. |
| 2012/0283169 A1 | 11/2012 | Grempler et al. |
| 2012/0296080 A1 | 11/2012 | Eckhardt et al. |
| 2013/0035281 A1 | 2/2013 | Klein et al. |
| 2013/0035298 A1 | 2/2013 | Broedl et al. |
| 2013/0064887 A1 | 3/2013 | Ito et al. |
| 2013/0096076 A1 | 4/2013 | Dugi et al. |
| 2013/0137646 A1 | 5/2013 | Wienrich et al. |
| 2013/0236543 A1 | 9/2013 | Ito et al. |
| 2013/0252908 A1 | 9/2013 | Mayoux et al. |
| 2014/0031301 A1 | 1/2014 | Eickelmann et al. |
| 2014/0038911 A1 | 2/2014 | Eickelmann et al. |
| 2014/0046046 A1 | 2/2014 | Eckhardt et al. |
| 2014/0087996 A1 | 3/2014 | Klein et al. |
| 2014/0088027 A1 | 3/2014 | Grempler et al. |
| 2014/0256624 A1 | 9/2014 | Grempler et al. |
| 2014/0303097 A1 | 10/2014 | Broedl et al. |
| 2014/0303098 A1 | 10/2014 | Broedl et al. |
| 2014/0315832 A1 | 10/2014 | Broedl et al. |
| 2015/0272977 A1 | 10/2015 | Reiche et al. |
| 2015/0322053 A1 | 11/2015 | Eckhardt et al. |
| 2016/0000816 A1 | 1/2016 | Broedl et al. |
| 2016/0030385 A1 | 2/2016 | Manuchehri et al. |
| 2016/0038523 A1 | 2/2016 | Broedl et al. |
| 2016/0038524 A1 | 2/2016 | Broedl et al. |
| 2016/0038525 A1 | 2/2016 | Broedl et al. |
| 2016/0074415 A1 | 3/2016 | Wienrich et al. |
| 2017/0020907 A1 | 1/2017 | Eickelmann et al. |
| 2017/0095424 A1 | 4/2017 | Ito et al. |
| 2017/0106009 A1 | 4/2017 | Mayoux |

FOREIGN PATENT DOCUMENTS

| | | |
|---|---|---|
| CA | 2402609 A1 | 9/2001 |
| CA | 2423568 A1 | 4/2002 |
| CA | 2437240 A1 | 8/2002 |
| CA | 2494177 A1 | 2/2004 |
| CA | 2496249 A1 | 3/2004 |
| CA | 2470365 A1 | 6/2004 |
| CA | 2508024 A1 | 6/2004 |
| CA | 2508226 A1 | 6/2004 |
| CA | 2526145 A1 | 9/2004 |
| CA | 2539032 A1 | 3/2005 |
| CA | 2548353 A1 | 7/2005 |
| CA | 2557269 A1 | 9/2005 |
| CA | 2557320 A1 | 9/2005 |
| CA | 2557801 A1 | 10/2005 |
| CA | 2569915 A1 | 1/2006 |
| CA | 2572149 A1 | 1/2006 |

(56) References Cited

FOREIGN PATENT DOCUMENTS

| | | |
|---|---|---|
| CA | 2572819 A1 | 1/2006 |
| CA | 2573777 A1 | 2/2006 |
| CA | 2574451 A1 | 2/2006 |
| CA | 2574500 A1 | 4/2006 |
| CA | 2649922 A1 | 11/2007 |
| CA | 2651019 A1 | 11/2007 |
| CA | 2720450 A1 | 10/2009 |
| CN | 1930141 A | 3/2007 |
| DE | 2758025 A1 | 7/1979 |
| DE | 2951135 A1 | 6/1981 |
| EP | 0206567 A2 | 12/1986 |
| EP | 1224195 B | 7/2002 |
| EP | 1344780 A1 | 9/2003 |
| EP | 1385856 A | 2/2004 |
| EP | 1553094 A1 | 7/2005 |
| EP | 1564210 A1 | 8/2005 |
| EP | 1609785 A1 | 12/2005 |
| EP | 1791852 A2 | 6/2007 |
| EP | 1803729 A1 | 7/2007 |
| EP | 1852108 A1 | 11/2007 |
| JP | 55007256 A | 1/1980 |
| JP | 56039056 A | 4/1981 |
| JP | 58164502 | 9/1983 |
| JP | 62030750 A | 2/1987 |
| JP | H1085502 A | 4/1998 |
| JP | 11124392 A | 5/1999 |
| JP | 2001288178 A | 10/2001 |
| JP | 2003511458 A | 3/2003 |
| JP | 2004196788 A | 7/2004 |
| JP | 2004359630 | 12/2004 |
| JP | 2005002092 A | 1/2005 |
| JP | 2005060625 A | 3/2005 |
| JP | 2006176443 A | 7/2006 |
| JP | 2008540373 A | 11/2008 |
| WO | 9831697 A1 | 7/1998 |
| WO | 0116147 A1 | 3/2001 |
| WO | 0127128 A1 | 4/2001 |
| WO | 0174834 A1 | 10/2001 |
| WO | 02064606 A1 | 8/2002 |
| WO | 2002064549 | 8/2002 |
| WO | 2002083066 A2 | 10/2002 |
| WO | 2003015769 | 2/2003 |
| WO | 2003020737 A1 | 3/2003 |
| WO | 2003031458 A1 | 4/2003 |
| WO | 2003064411 | 8/2003 |
| WO | 2003078404 A1 | 9/2003 |
| WO | 2003099836 A1 | 12/2003 |
| WO | 2004007517 A1 | 1/2004 |
| WO | 2004013118 A1 | 2/2004 |
| WO | 2004018468 A2 | 3/2004 |
| WO | 2004046115 A1 | 6/2004 |
| WO | 2004052902 A1 | 6/2004 |
| WO | 2004052903 A1 | 6/2004 |
| WO | 2004063209 A2 | 7/2004 |
| WO | 2004076470 A2 | 9/2004 |
| WO | 2004080990 A1 | 2/2005 |
| WO | 2005011592 A2 | 2/2005 |
| WO | 2005012318 A2 | 2/2005 |
| WO | 2005012326 A1 | 2/2005 |
| WO | 2005021566 A2 | 3/2005 |
| WO | 2005063785 A2 | 7/2005 |
| WO | 2005085237 A1 | 9/2005 |
| WO | 2005085265 A1 | 9/2005 |
| WO | 2005092877 A1 | 10/2005 |
| WO | 2006002912 A1 | 1/2006 |
| WO | 2006006496 A1 | 1/2006 |
| WO | 2006008038 A1 | 1/2006 |
| WO | 2006010557 A1 | 2/2006 |
| WO | 2006011469 A1 | 2/2006 |
| WO | 2006018150 A1 | 2/2006 |
| WO | 2006034489 A2 | 3/2006 |
| WO | 2006037537 A2 | 4/2006 |
| WO | 2006064033 A2 | 6/2006 |
| WO | 2006089872 A1 | 8/2006 |
| WO | 2006108842 A1 | 10/2006 |
| WO | 2006117359 A1 | 11/2006 |
| WO | 2006117360 A1 | 11/2006 |
| WO | 2006120208 A1 | 11/2006 |
| WO | 2007000445 A1 | 1/2007 |
| WO | 2007014894 A2 | 2/2007 |
| WO | 2007025943 A2 | 3/2007 |
| WO | 2007028814 A1 | 3/2007 |
| WO | 2007031548 A2 | 3/2007 |
| WO | 2007039417 A1 | 4/2007 |
| WO | 2007041053 A2 | 4/2007 |
| WO | 2007093610 A1 | 8/2007 |
| WO | 2007128724 A1 | 11/2007 |
| WO | 2007128749 A1 | 11/2007 |
| WO | 2007128761 A2 | 11/2007 |
| WO | 2007144175 A2 | 12/2007 |
| WO | 2008002905 A2 | 1/2008 |
| WO | 2008020011 A1 | 2/2008 |
| WO | 2008022267 A2 | 2/2008 |
| WO | 2008034859 A1 | 3/2008 |
| WO | 2008049923 A1 | 5/2008 |
| WO | 2008055870 A1 | 5/2008 |
| WO | 2008055940 A2 | 5/2008 |
| WO | 2008062273 A2 | 5/2008 |
| WO | 2008089892 A1 | 7/2008 |
| WO | 2008090210 A1 | 7/2008 |
| WO | 2008101938 A1 | 8/2008 |
| WO | 2008101939 A1 | 8/2008 |
| WO | 2008101943 A1 | 8/2008 |
| WO | 2008116179 A1 | 9/2008 |
| WO | 2008116195 A2 | 9/2008 |
| WO | 2008131149 A2 | 10/2008 |
| WO | 200022010 A1 | 2/2009 |
| WO | 2009022007 A1 | 2/2009 |
| WO | 2009035969 A1 | 3/2009 |
| WO | 2009091082 A1 | 7/2009 |
| WO | 2009099734 A1 | 8/2009 |
| WO | 2009121945 A2 | 10/2009 |
| WO | 2010045656 A2 | 4/2010 |
| WO | 2010092123 A1 | 8/2010 |
| WO | 2010092124 A1 | 8/2010 |
| WO | 2010092125 A1 | 8/2010 |
| WO | 2010092126 A1 | 8/2010 |
| WO | 2010119990 A1 | 10/2010 |
| WO | 2010138535 A1 | 12/2010 |
| WO | 2011039107 A1 | 4/2011 |
| WO | 2011039108 A2 | 4/2011 |
| WO | 2011039337 A1 | 4/2011 |
| WO | 2011060290 A2 | 5/2011 |
| WO | 2011120923 A1 | 10/2011 |
| WO | 2012031124 A2 | 3/2012 |
| WO | 2012062698 A1 | 5/2012 |
| WO | 2012106303 A1 | 8/2012 |
| WO | 2012107476 A1 | 8/2012 |
| WO | 2012120040 A1 | 9/2012 |
| WO | 2013007557 A1 | 1/2013 |
| WO | 2013131967 A1 | 9/2013 |
| WO | 2013139777 A1 | 9/2013 |

OTHER PUBLICATIONS

Neamati, Ouri., et al;, "Depsides and Depsidones as Inhibiton of HIV-1 Integrase: Dimvery of Novel Inhibitors Through 3D Database Searclung", J. Med. Chem., 1997, vol. 40, pp. 942-951.

Nobre, Sabrina M., et al; Synthesis of Diarylmethane Derivatives from Pd-Catalyzed Cross-Coupling Reactions of Benzylic Halides with Arylboronic Acids; Tetrahedron Letters (2004) vol. 45 8225-8228.

Non Final Office Action dated Apr. 2, 2008 from U.S. Appl. No. 11/674,839, filed Feb. 14, 2007.

Non Final Office Action dated Apr. 2, 2008 from U.S. Appl. No. 11/742,612, filed May 1, 2007.

Non-Final Office Action dated Jun. 24, 2008 from U.S. Appl. No. 11/406,971, filed Apr. 19, 2006.

Non-Final Office Action dated Jun. 5, 2008 from U.S. Appl. No. 11/408,899, filed Apr. 21, 2006.

Non-Final Office Action dated May 8, 2008 from U.S. Appl. No. 11/359,846, filed Feb. 22, 2006.

Notice of Allowance and Fee(s) Due dated Jan. 13, 2009 from U.S. Appl. No. 11/304,284, filed Dec. 15, 2005.

(56) References Cited

OTHER PUBLICATIONS

Notice of Allowance and Fee(s) Due dated Dec. 30, 2008 from U.S. Appl. No. 11/674,839, filed Feb. 14, 2007.
Notice of Allowance and Fee(s) Due dated Feb. 3, 2009 from U.S. Appl. No. 11/359,846, filed Feb. 22, 2006.
Notice of Allowance and Fee(s) Due dated Jan. 2, 2009 from U.S. Appl. No. 11/742,612, filed May 1, 2007.
Oku, Akira., et al; T-1095, An Inhibitor or renal Na+ -Glucose Cotransporters, May Provide a Novel Approach to Treating Diabetes; Diabetes (1999) vol. 48 pp. 1794-1800.
Panchapakesan, Usha et al. Effects of SGLT2 Inhibition in Human Kidney Proximal Tubular Cells—Renoprotection in Diabetic Nephropathy? PLOS one, (2013) vol. 8, Issue 2, e54442, 8 pgs.
Patil, Basanagouda M. et al. "Elevation of systolic blood pressure in an animal model of olanzapine induced weight gain" (2006) European Journal of Pharmacology, vol. 551, pp. 112-115.
Perner, Richard J., et al; 5,6,7-Trisubstituted 4-Aminopyrido[2,3-d]pyrimidines as Novel inhibitors of Adenosine Kinase; Journal of Medicinal Chemistry (2003) vol. 46 pp. 5249-5257.
Piya, Milan K. et al. "Emerging treatment options for type 2 diabetes" British Journal of Clinical Pharmacology, (2010) vol. 70, No. 5, pp. 631-644.
Powers, Richard E. et al. "Understanding the Side Effects of Neuroleptics" (2008) Bureau of Geriatric Psychiatry/DETA, pp. 17-24.
Printz, Richard L. et al. "Tweaking the Glucose Sensor: Adjusting Glucokinase Activity with Activator Compounds" Endocrinology, (2005) vol. 146, No. 9, pp. 3693-3695.
Rainier, Jon D. et al. "Aluminum- and Boron-Mediated C-Glycoside Synthesis from 1,2-Anhydroglycosides" Organic Letters, (2000) vol. 2, No. 17, pp. 2707-2709.
Randzio, Stanislaw L. et al. "Metastability and Instability of Organic Crystalline Substances" J. Phys. Chem. (2008) 112, pp. 1435-1444.
Redenti, Enrico et al. "Drug/Cyclodextrin/Hydroxy Acid Multicomponent Systems. Properties and Pharmaceutical Applications" Journal of Pharmaceutical Sciences, (2000) vol. 89, No. 1, pp. 1-8.
Response dated Nov. 5, 2008 to Non-Final Office Action dated May 8, 2008 from U.S. Appl. No. 11/359,846, filed Feb. 22, 2006.
Response dated Sep. 25, 2008 to Non-Final Office Action dated Apr. 2, 2008 from U.S. Appl. No. 11/674,839, filed Feb. 14, 2007.
Response dated Sep. 25, 2008 to Non-Final Office Action dated Apr. 2, 2008 from U.S. Appl. No. 11/742,612, filed May 1, 2007.
Revesz, Lasslo., et al; SAR of Benzoylpylpyridines and Benzophenones as p38 Alpha MAP Kinase Inhibitors with Oral Activity; Bioorganic & Medicinal Chemistry Letters (2004) vol. 14 pp. 3601-3605.
Rieusset, Jennifer et al. "Insulin Acutely Regulates the Expression of the Peroxisome Proliferator-Activated Receptor -y in Human Adipocytes" (1999) Diabetes, vol. 48, pp. 699-705.
Ritchie, C.W. et al. "The impact upon extra-pyramidal side effects, clinical symptoms and quality of life of a switch from conventional to atypical antipsychotics (risperidone or olanzapine) in elderly patients with schizophrenia" (2003) International Journal of Geriatric Psychiatry, vol. 18, pp. 432-440.
Rudnic, Edward et al. "Oral Solid Dosage Forms" Remington's Pharmaceutical Sciences, 18th Ed, Gennaro, A.R. Ed, Made Pub. Co. (1990) pp. 1633-1665.
Shannon, James A. et al. "The Excretion of Inulin, Xylose and Urea by Normal and Phlorizinized Man" New York University College of Medicine, Department of Physiology, Feb. 13, 1935, 393-401.
Sherwin, Robert S. et al. "The Prevention or Delay of Type 2 Diabetes" Diabetes Care, (2002) vol. 25, No. 4, pp. 742-749.
Singhal, Dharmendra et al. "Drug polymorphism and dosage form design: a practical perspective" Advanced Drug Delivery Reviews, 56, (2004) pp. 335-347.
Sommer, Michael Bech., et al; displacement of Halogen of 2-Halogen-Substituted Benzonitriles with Carbonions. Preparation of (2-Cyanoaryl)arylacetonitriles; Journal of Organic Chemistry (1990) vol. 55 pp. 4817-4821.
Stazi, Federica., et al; Statistical Experimental Design-Driven Discovery of room-Temperature Conditions for Palladium-Catalyzed Cyanation of Aryl Bromides; Tetrahedron Letters (2005) vol. 46 1815-1818; Elsevier Ltd.
Stella, Valentino J. "Prodrugs as therapeutics" (2004) Ashley Publications, vol. 14, No. 3, pp. 277-280.
Svegliati-Baroni, Gianluca et al. "Glucagon-like peptide-1 receptor activation stimulates hepatic lipid oxidation and restores hepatic signalling alteration induced by a high-fat diet in nonalcholic steatohepatitis" (2011) Liver International, vol. 31, 9, pp. 1285-1297.
Tanaka, Chikako "Therapeutic Drugs for Metabolic Diseases, Chapter 2" (2002) New Yakurigaku (New Pharmacology) pp. 524-527.
Testa, Bernard "Prodrug research: futile or fertile?" (2004) Biochemical Pharmacology vol. 68, pp. 2097-2106.
Thomas, Leo et al. "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor, Has a Superior Potency and Longer Duration of Action Compared with Other Dipeptidyl Peptidase-4 Inhibitors" Journal of Pharmacology and Experimental Therapeutics (2008) 325, pp. 175-182.
Thomson, Scott C. et al. "Acute and chronic effects of SGLT2 blockade on glomerular and tubular function in the early diabetic rat" (2011) Am J Physiol Regul Integr Comp Physiol, V 302, pp. R75-R83.
Threlfall, Terry "Structural and Thermodynamic Explanations of Ostwald's Rule" Organic Process Research & Development (2003) vol. 7, pp. 1017-1027.
Tsujihara, Kenji et al. "Na+-Glucose Cotransporter (SGLT) Inhibitors as Antidiabetic Agents. 4. Synthesis and Pharmacological Properties of 4'-Dehydroxyphlorizin Derivatives Substituted on the B Ring" J. Met Chem. (1999) vol. 42, pp. 5311-5324.
Tykwinski, Rik R; Evolution in the Palladium-Catalyzed Cross-Coupling of sp- and sp2-Hybridized Carbon Atoms; Angew Chemical International Edition (2003) vol. 42 pp. 1566-1568.
Ueta, Kiichiro., et al; Long-Term Treatment with the Na+-Glucose Cotransporter Inhibitor T-1095 Causes Sustained Improvement in Hyperglycemia and Prevents Diabetic Neuropathy in Goto-Kakizaki Rats; Life Sciences (2005) vol. 76 pp. 2655-2668.
Unknown "Intensification of Development of SGLT inhibitor—New Alternative of Antidiabetic" Aug 21, 2007; 2 pgs; http://www.yakuji.co.jp/entry4100.html.
USPTO, U.S. Appl. No. 14/805,838, Third-party submission under 37 CFR 1.290 dated Dec. 12, 2016. 19 pgs.
Vallon, Volker et al. "Glomerular Hyperfiltration in Experimental Diabetes Melliutes: Potential Role of Tubular Reabsorption" (1999) J. Am. Soc. Nephrol., V 10: pp. 2569-2576.
Vallon, Volker et al. "SGLT2 inhibitor empagliflozin reduces renal growth and albuminuria in proportion to hyperglycemia and prevents glomerular hyperfiltration in diabetic Akita mice" (2013) Am J Physiol Renal Physiol, 306, F194-F204.
Vervoort, G. et al. "Glomerular hyperfiltration in type 1 diabetes mellitus results from primary changes in proximal tubular sodium handling without changes in volume expansion" (2005) European Journal of Clinical Investigation vol. 35, pp. 330-336.
Wallace, Debra J., et al; Cyclopropylboronic Acid: Synthesis and Suzuki Cross-Coupling Reactions; Tetrahedron Letters (2002) vol. 43 pp. 6987-6990; Pergamon Press.
Abstract ASN09L1_307a "Contact View (TH-P0751) Kidney Function and Response to Diabetes in Mice Lacking SGLT2", Vallon, Volker et al, Oct. 29, 2009, 1 pg.
Abstract ASN09L1_4153a, "Contact View (SA-P02723) Chronic SGLT2 Blockade Reduces Proximal Reabsorption and Normalizes State of Tubuloglomerular Feedback Activation in Hyperfiltering Diabetic Rats" Thomson, Scott et al., Oct. 31, 2009, 1 pg.
Adachi et al., Metabolism, vol. 49, No. 8, 2000 pp. 990-995.

(56) References Cited

OTHER PUBLICATIONS

Adachi, Tetsuya., et al; T-1095, A Renal Na+-Glucose Transporter Inhibitor, Improves Hyperglycemia in Streptozotocin-Induced Diabetic Rats; Metabolism (2000) vol. 49 No. 8 pp. 990-995.
American Diabetes Association "Consensus Development Conference on Antipyschotic Drugs and Obesity and Diabetes" (2004) Diabetes Care, vol. 27, No. 2, pp. 596-601.
American Diabetes Association "Diagnosis and Classification of Diabetes Mellitus" Diabetes Care, vol. 33, Supplement 1, Jan. 2010. pp. S62-S69.
Anonymous "Efficacy and Safety of Empagliflozin (BI 10773) in Patients with Type 2 Diabetes and Renal Impairment" Jan. 8, 2013, XP055120166, www.clinicaltrials.gov/ct2/show/study/NCT01164501?term=empagliflozin&rank=26.
Anonymous "Prevalence of Chronic Kidney Disease and Associated Risk Factors—United States, 1999-2004", Mar. 2, 2007, XP055119515, http://www.cdc.gov/mmwr/preview/mmwrhtml/mm5608a2.htm.
Ault Addison, "Techniques and experiments for organic chemistry" University Science Books, 1998, pp. 59-60.
Banker, Gilbert S. et al. "Modern Pharmaceutics, Third Edition, Revised and Expanded" (1996) Marcel Dekker, p. 596.
Baptista, Trino et al. "Pharmacological Management of Atypical Antipsychotic-Induced Weight Gain" (2008) CNS Drugs, 22, 6, pp. 478-495.
Barnett, Anthony H. et al. "Efficacy and safety of empagliflozin added to existing antidiabetes treatments in patients with type 2 diabetes and chronic kidney disease: a randomised, double-blind, placebo-controlled trial" The Lancet, (2014) vol. 2, pp. 369-384.
Benhaddou, Rachida., et al; Tetra-n-Propylammonium Tetra-Oxoruthenate(VII): A Reagent of Choice for the Oxidation of Diversely Protected Glycopyranoses and Glycofuranoses to Lactones; Carbohydrate Research (1994) vol. 260 pp. 243-250.
Bloomgarden, Zachary T. "Diabetes Treatment" Diabetes Care, (Mar. 2009) vol. 32, No. 3 pp. e25-e30.
Boyda, Heidi N et al. "Preclinical models of antipsychotic drug-induced metabolic side effects"(2010) Trends in Pharmacological Sciences vol. 31, pp. 484-497.
Buhler, Volker "Kollidon ® Polyvinylpyrrolidone excipients for the pharmaceutical industry" 9th revised edition, Mar. 2008, 1-331.
Busch, Frank R. et al. "Grignard Reagents—Industrial Applications and Strategy", Grignard Reagents, New Developments, John Wiley & Sons Ltd, copyright (2000), pp. 165-183.
Byrn, Stephen et al. "Pharmaceutical Solids: A Strategic Approach to Regulatory Considerations" Pharmaceutical Research, vol. 12, No. 7, (1995) pp. 945-954.
Castelhano, Arlindo L. et al. "Reactions of an Electrophilic Glycine Cation Equivalent With Grignard Reagents a Simple Synthesis of β,g-Unsaturated Amino Acids" (1986) Tetrahedron Letters, vol. 27, No. 22, pp. 2435-2438.
Cernea Simona. et al. "β-Cell Protection and Therapy for Latent Autoimmune Diabetes in Adults" Diabetes Care (2009) vol. 32, Supplement 2, pp. S246-S252.
Deacon, Carolyn F. "Perspectives in Diabetes Therapeutic Strategies Based on Glucagon-Like Peptide 1" Diabetes, (2004) vol. 53 pp. 2181-2189.
Diabetes Mellitus, Merck Manual Online Edition, (retrieved Sep. 13, 2011) http://www.merckmanuals.com/professional/endocrine_and_metabolic_disorders/diabetes_mellitus_and_disorders_of_carbohydrate_metabolism/diabetes_mellitus_dm.html#v987998. Revision Jun. 2008.
Dohle, Wolfgang., et al; Copper-Mediated Cross-Coupling of Functionalized Arylmagnesium Reagents with Functionalized Alkyl and Benzylic Halides; Organic Letters (2001) vol. 3 No. 18 pp. 2871-2873.
Drug Watch "Type 2 Diabetes Mellitus" Formulary vol. 43 Aug. 2008 p. 304.
Eade: Ronald E. "Extractives of Australian Timbers. XV* THe Synthesis of 7,4'-Di-O-methylbayin" (1975) Austr. J. Chemistry, vol. 28, pp. 2011-2018.

Ellinger, Lara K. et al. "Efficacy of Meflormin and Topiramate in Prevention and Treatment of Second-Generation Antipsychotic-Induced Weight Gain" Annals of Pharmacotherapy (2010) vol. 44, No. 4, pp. 668-679.
Embase Database. Accession No: 0050872772. Jelsing, J et al. "Empagliflozin a novel sodium glucose cotransporter-2 inhibitor improves glucose homeostasis and preserves pancreatic beta cell mass in db/db mice" (2012) 2 pgs.
Embase database: Accession No. 0050781595. Jelsing, Jacob et al. "The sodium glucose cotransporter-2 (SGLT-2) inhibitor empagliflozin has a durable effect on the restoration of glucose homeostasis by preserving beta-cell mass in zucker diabetic fatty rats" (2012) 2 pgs.
Ettmayer, Peter et al. "Lessons Learned from Marketed and Investigational Prodrugs" (2004) Journal of Medicinal Chemistry, vol. 47, No. 10, pp. 2393-2404.
Ferrannini, Ele et al. "CV Protection in the EMPA-REG OUTCOME Trial: A "Thrifty Substrate" Hypothesis" Diabetes Care, Jun. 11, 2016, pp. 1-7.
Fuerstner, Alois., et al; Practical Method for the Rhodium-Catalyzed Addition of Aryl- and Alkenylboronic Acids to Aldehydes; Advanced Synthesis and Catalysis (2001) vol. 343 No. 4 pp. 343-350.
Fujimori, Yoshikazu et al. "Remogliflozin Etabonate in a Novel Category of Selective Low-Affinity Sodium Glucose Cotransporter (SGLT2) Inhibitors, Exhibits Antidiabetic Efficacy in Rodent Models" (2008) Journal of Pharmacology and Experimental Therapeutics vol. 327 No. 1, pp. 268-276.
Ghassemi et al. "Synthesis and properties of new sulfonated poly(p-phenylene) derivatives for proton exchange membranes" Polymer (2004) pp. 5847-5854.
Goodwin, Nicole C. et al. "Novel L-Xylose Derivatives as Selective Sodium-Dependent Glucose Cotransporter 2 (SGLT2) Inhibitors for the Treatment of Type 2 Diabetes" (2009) Journal Medicinal Chemistry vol. 52 pp. 6201-6204.
Graefe-Mody, Eu., et al., "Evaluation of the potential for steady-state pharmacokinectic and pharmacodynamic interactions between the DPP-4 inhibitor linagliptin and metformin in healthy subjects". Current Medical Research and Opinion, Informa Healthcare, GB, vol. 25. No. 8, Aug. 1, 2009, pp. 1963-1972.
Greco, Gary T. et al. "Segregation of Active Constituents from Tablet Formulations During Grinding: Theoretical Considerations" Drug Development and Industrial Pharmacy, (1982) 8(4), pp. 565-578.
Hasnain, Mehrul et al. "Metformin for Atypical Antipsychotic-Induced Weight Gain and Glucose Metabolism Dysregulation—Review of Literature and Clinical Suggestions" (2010) CNS Drugs, 24(3), pp. 194-206.
Hatsuda, Asanori., et al; A Practical Synthesis of Highly Functionalized Aryl Nitriles Through Cyanation of Aryl Bromides Employing Heterogeneous Pd/C; Tetrahedron Letters (2005) vol. 46 pp. 1849-1853; Elsevier Ltd.
Henderson, David C. et al. "Clozapine and Hypertension: A Chart Review of 82 Patients" (2004) J Clin Psychiatry, 65, pp. 686-689.
Hussey, Elizabeth K. et al. "Safety, Pharmacokinetics and Pharmacodynamics of Remogliflozin Etabonate (SGLT2 Inhibitor) and Metformin When Co-Administered in Type 2 Diabetes Mellitus (T2DM) Patients" Diabetes, American Diabetes Association, (2009) XP00913667, vol. 58, p. A157.
Hutton, Craig A., et al; A Convenient Preparation of dityrosine Via Miyaura Borylation-Suzuki Coupling of Iodotyrosine Derivatives; Tetrahedron Letters (2003) vol. 44 pp. 4895-4898; Pergamon Press.
Ilda, Takehiko., et al; Tributylmagnesium Ate Complex-Mediated Novel Bromine-Magnesium Exchange Reaction for Selective Monosubstitution of Dibromoarenes; Tetrahedron Letters (2001) vol. 42 pp. 4841-4844; Pergamon Press.
International Search Report and Written Opinion for PCT/EP2012/062922 dated Aug. 14, 2012.
International Search Report for PCT/EP2005/002618 dated Jun. 30, 2005.
International Search Report for PCT/EP2005/056806 dated Dec. 27, 2006.

(56) References Cited

OTHER PUBLICATIONS

International Search Report for PCT/EP2006/061520 dated Jul. 26, 2006.
International Search Report for PCT/EP2006/061956 dated Jul. 5, 2006.
International Search report for PCT/EP2006/061957 dated Jul. 5, 2006.
International Search Report for PCT/EP2006/062191 dated Aug. 8, 2006.
International Search Report for PCT/EP2006/064702 dated Jul. 26, 2007.
Wang Y et al: "BI-1356. Dipeptidyl-peptidase IV inhibitor, antidiabetic agent" Drugs of the Future, Prods Science, ES,vol. 33, No. 6, Jun. 1, 2008, pp. 473-477.
Websters Third New International Dictionary, Editor: Gove, definition of prevent; 1963, 2 pgs.
Wolff, Manfred E., et al., "Burger's Medicinal Chemistry and Drug Discovery, Fifth Edition, vol. 1, Principles and Practices", (1995) Wiley-Interscience Publication pp. 975-977.
Woo, Young Sup et al. "Blood pressure changes during clozapine or olanzapine treatment in Korean schizophrenic patients" (2009) The World Journal of Biological Psychiatry, vol. 10(4); pp. 420-425.
Wu, Ren-Rang et al. "Lifestyle Intervention and Metformin for Treatment of Antipsychotic-Induced Weight Gain, A Randomized Controlled Trial" Journal of American Medical Association (2008) V 299, pp. 185-193.
Xue, Song., et al; Zinc-mediated Synthesis of Alpha-C-Glycosided from 1,2-Anhydroglycosides; Synletters (2003) vol. 6 pp. 870-872.
Yamada, Yuichiro et al. "Clinic: Careful Progress in the Field and new Therapeutic Methods" Medical Medical Online, (2007) vol. 220, No. 13, pp. 1219-1221.
Yao, Chun-Hsu et al. "Discovery of Novel N-b-D-Xylosylindole Derivatives as Sodium-Dependent Glucose Cotransporter 2 (SGLT2) Inhibitors for the Management of Hyperglycemia in Diabetes" (2011) J. Met Chem. vol. 54, pp. 166-178.
Zhang, L. et al "Dapagliflozin treatment in patients with different stages of type 2 diabetes mellitus: effects on glycaemic control and body weight" Diabetes, Obesity and Metabolism (2010) vol. 12, No. 6, p. 510-515.
International Search Report for PCT/EP2006/065710 dated Mar. 8, 2007.
International Search Report for PCT/EP2006/066107 dated Jan. 11, 2007.
International Search Report for PCT/EP2006/066347 dated Mar. 7, 2007.
International Search Report for PCT/EP2007/051411 dated May 2, 2007.
International Search Report for PCT/EP2007/054248 dated Jun. 18, 2007.
International Search Report for PCT/EP2007/062023 dated Sep. 17, 2008.
International Search Report for PCT/EP2010//064117 dated Nov. 30, 2010.
International Search Report for PCT/EP2010/051734 dated Jun. 8, 2010.
International Search Report for PCT/EP2010/051735 dated May 20, 2010.
International Search Report for PCT/EP2010/051736 dated May 7, 2010.
International Search Report for PCT/EP2010/051737 dated May 7, 2010.
International Search Report for PCT/EP2010/064120 dated Mar. 31, 2011.
International Search Report for PCT/EP2010/064619 dated Jan. 20, 2011.
International Search Report for PCT/EP2011/054734 dated Aug. 12, 2011.
International Search Report for PCT/EP2011/069532 dated Dec. 15, 2011.
International Search Report for PCT/EP2012/052108 dated Mar. 8, 2012.
International Search Report for PCT/EP2012/053910 dated May 14, 2012.
International Search Report for PCT/EP2012/060194 dated Jul. 17, 2012.
International Search Report for PCT/EP2013/054524 dated May 6, 2013.
International Search Report for PCT/EP2013/055671 dated Apr. 16, 2013.
International Search Report for PCT/EP2014/056655 dated Apr. 3, 2014.
International Search Report for PCT/EP2014/056657 dated Apr. 3, 2014.
International Search Report for PCT/EP2014/057754 dated Apr. 16, 2014.
International Search Report for PCT/EP2014/057754 dated May 27, 2014.
Isaji, Masayuki "Sodium-glucose cotransporter inhibitors for diabetes"Current Opinion in Investigational Drugs, (2007) vol. 8, No. 4, pp. 285-292.
Jabbour, Serge A. "The Importance of Reducing Hyperglycemia While Preserving Insulin Secretion—The Rational for Sodium-coupled Glucose Co-trnasporter 2 Inhibition in Diabetes" Touch Briefings, US Endocrinology (2009) pp. 75-78.
Jagdmann Jr, G. Erik ; Synthesis of 5-(4-Substituted Benzyl)-2,4-Diaminoquinazolines as Inhibitors of Candida Albicans Dihydrofolate Reductase; Journal Heterocyclic Chemical (1995) vol. 32 pp. 1461-1465.
Jones, Byrony "Empagliflozin—one step closer to glycaemic control in patients with type II diabetes and CKD?" (2014) Nature Reviews Nephrology 10, 181, 2 pgs.
Joshi, Shashank R. "Metformin: Old Wine in New Bottle—Evolving Technology and Therapy in Diabetes" Journal of Association of Physicians in India, (2005) vol. 53, pp. 963-972.
Kadowaki, T et al. "PPAR gamma agonist and antagonist" Nihon Yakurigaku Zasshi (2001) vol. 118, No. 9, pp. 321-326. (English abstract).
Kasichayanula, Sreeneeranj et al. "The Influence of Kidney Function on Dapagliflozin Exposure, Metabolism and Pharmacodynamics in Healthy Subjects and in Patients with Type 2 Diabetes Mellitus" (2012) British Journal of Clinical Pharmacology, vol. 76, Issue 3, pp. 432-444.
Knochel, Paul et al. "Highly functionalized Organomagnesium Reagents Prepared through Halogen-Metal Exchange" Angew. Chem. INt. Ed. (2003) vol. 42, 4302-4320.
Koo, Ja Seo., et al; 2-Pyridyl Cyanate: A Useful Reagent for he Preparation of Nitriles; Synthetic Communications (1996) vol. 26 No. 20 pp. 3709-3713; Marcel Dekker, Inc.
Kuribayashi, Takeshi., et al; Bis C-Glycosylated Diphenylmethanes for Stable Glycoepitope Mimetics; Syntletters (1999) vol. 6 pp. 737-740.
Kuribayashi, Takeshi., et al; c-Glycosylated Aryl tins: Versatile Building Blocks for Aryl C-Glycoside Glycomimetics; J. Carbohydrate Chemistry (1999) vol. 18, No. 4 pp. 371-382.
Kuribayashi, Takeshi., et al; C-Glycosylated Diphenylmethanes and Benzophenones: The Stille Coupling Reaction of C-Glycosylated Aryl tins with Benzyl Bromides and Acid Chlorides; J. Carbohydrate Chemistry (1999) vol. 18, No. 4 pp. 393-401.
Langle, Sandrine., et al; Selective Double Suzuki Cross-Coupling Reactions. Synthesis of Unsymmetrical Diaryl (or Heteroaryl) Methanes; Tetrahedron Letters (2003) vol. 44 pp. 9255-9258; Pergamon Press.
Lehmann, Ule et al. "Palladium-Catalyzed Cross-Coupling Reactions between Dihydropyranylindium Reagents and Aryl Halides, Synthesis of C-Aryl Glycals" Organic Letters, 2003, vol. 5, No. 14, pp. 2405-2408.
Li, T, et al. "Lack of Pharmacokinetic Interaction between Dapagliflozin and Pioglitazone in Healthy Subjects" Journal of Clinical Pharmacology, (2009) vol. 49, No. 9, pp. 1093.
Lieberman, Joseph A. "Metabolic Changes Associated with Antipsychotic Use" Prim Care Companion J Clinc Psychiatry (2004) 6, pp. 8-13.

(56) References Cited

OTHER PUBLICATIONS

Lipworth, Brian J. "Clinical pharmacology of b3-adrenoceptors" Br J Clin Pharmacol (1996) pp. 291-300.
Maayan, Lawrence et al. "Effectiveness of Medications Used to Attenuate Antipsychotic-Related Weight Gain and Metabolic Antipsychotic-Related Weight Gain and Metabolic Abnormalities: A Systematic Review and Meta-Analysis" (2010) Neuropsychopharmacology, vol. 35, pp. 1520-1530.
Magee, G.M. et al. "Is hyperfiltration associated with the future risk of developing diabetic nephropathy? A meta-analysis" Diabetologia (2009) 52: pp. 691-697.
Malatiali, Slava et al. "Phlorizin Prevents Glomerular Hyperfiltration but not Hypertrophy in Diabetic Rats" (2008) Experimental Diabetes Research, vol. 2008, 7 pgs.
McLaughlin, Mark, et al; Suzuki-Miyaura Cross-Coupling of Benzylic Phospahates with Arylboronic Acids; Organic Letters (2005) vol. 7 No. 22 pp. 4875-4878.
McMaster University, Chem2006 Lab Manual, 1997/98, Expt 1, Part B, pp. 1-9.
Meng, Wei et al "Discovery of Dapagliflozin: A Potent, Selective Renal Sodium-Dependent Glucose Cotransporter 2 (SGLT2) Inhibitor for the Treatment of Type 2 Diabetes" J. Med. Chem. (2008) vol. 51, pp. 1145-1149.
Merck Manual Online Edition, "Diabetes Mellitus" http://www.merckmanuals.com/professional/endocrine_and_metabolic_disorders/diabetes_mellitus_and_disorders of carbohyrate_metabolism/diabetes_mellitus_dm.html#v987998. last revision Jun. 2008 by Preeti Kishore M.D.
Merriam-Webster's Collegiate Dictionary,definition of prevent, published 1998 by Merriam-Webster Inc. p. 924.
Miller, Del D. "Review and Management of Clozapine Side Effects"(2000) J Clinc Psychiatry, 61 (Suppl 8) pp. 14-17.

\* cited by examiner

PROCESSES FOR PREPARING OF GLUCOPYRANOSYL-SUBSTITUTED BENZYL-BENZENE DERIVATIVES

The present invention relates to a process for preparing of glucopyranosyl-substituted benzyl-benzene derivatives of the formula III,

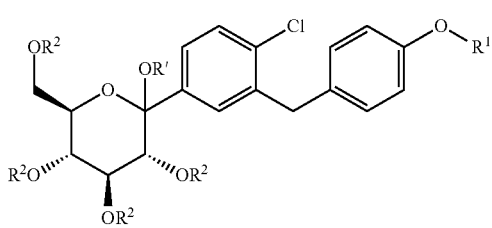

wherein the substituents $R^1$ and, $R^2$ and R' are defined as hereinafter. Furthermore the present invention relates to processes for preparing intermediates and starting materials of the process for preparing of glucopyranosyl-substituted benzyl-benzene derivatives. In addition the present invention relates to uses of the processes according to the invention.

BACKGROUND OF THE INVENTION

In WO 2005/092877 glucopyranosyl-substituted benzene derivatives of the general formula

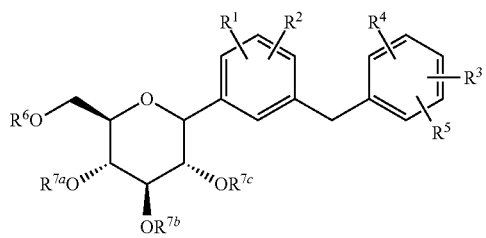

wherein the groups $R^1$ to $R^6$ and $R^{7a}$, $R^{7b}$, $R^{7c}$ are as defined therein, are described. Such compounds have a valuable inhibitory effect on the sodium-dependent glucose cotransporter SGLT, particularly SGLT2.

In WO 2006/117359 a crystalline form of 1-chloro-4-(β-D-glucopyranos-1-yl)-2-[4-((S)-tetrahydrofuran-3-yloxy)-benzyl]-benzene and its synthesis is described.

In WO 2006/120208 several methods of synthesis of compounds of the formula

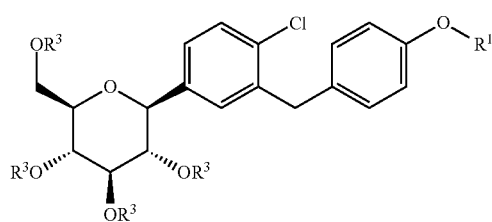

wherein $R^1$ denotes cyclobutyl, cyclopentyl, cyclohexyl, R-tetrahydrofuran-3-yl, S-tetrahydrofuran-3-yl or tetrahydropyran-4-yl are described. The example XVIII therein relates to the synthesis of 1-chloro-4-(β-D-glucopyranos-1-yl)-2-(4-(S)-tetrahydrofuran-3-yloxy-benzyl)-benzene.

According to the variant E therein (S)-3-[4-(5-iodo-2-chloro-benzyl)-phenoxy]-tetrahydrofuran is reacted with i-PrMgCl/LiCl in THF at low temperatures to form an organometallic intermediate. In an aqueous quenching step an aqueous $NH_4Cl$ solution (25 weight-%) is added. After the addition of methyl-tertbutylether the organic layer comprising the intermediate product is separated. In attempts to upscale this process it was observed that the separation of the aqueous and the organic phase may cause difficulties, for example by the formation of three phases.

AIM OF THE INVENTION

The aim of the present invention is to find advantageous processes for preparing of glucopyranosyl-substituted benzyl-benzene derivatives of the formula III; in particular robust processes with which the product may be obtained in high yields, high enantiomeric or diastereomeric purity and which allow the manufacture of the product in a commercial scale with a low technical expenditure and a high space/time yield.

Another aim of the present invention is to find a commercially viable process for preparing of glucopyranosyl-substituted benzyl-benzene derivatives of the formula III comprising an aqueous quenching step which allows a reliable and easy separation of the aqueous and the organic phase.

Another aim of the present invention is to provide processes for preparing the starting materials of the before mentioned method of manufacture.

Other aims of the present invention will become apparent to the skilled artisan directly from the foregoing and following description.

OBJECT OF THE INVENTION

In a first aspect the present invention relates to a process for preparing a glucopyranosyl-substituted benzyl-benzene derivative of general formula III,

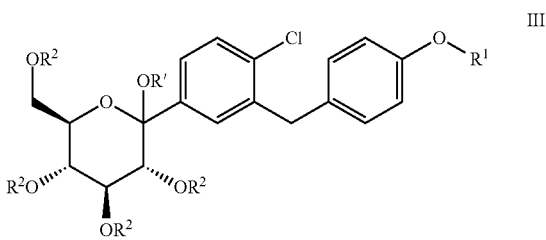

wherein
$R^1$ denotes $C_{1-3}$-alkyl, cyclobutyl, cyclopentyl, cyclohexyl, (R)-tetrahydrofuran-3-yl, (S)-tetrahydrofuran-3-yl or tetrahydropyran-4-yl; and
$R^2$ independently of one another denote hydrogen, ($C_{1-8}$-alkyl)carbonyl, ($C_{1-8}$-alkyl)oxycarbonyl, phenylcarbonyl, phenyl-($C_{1-3}$-alkyl)-carbonyl, phenyl-$C_{1-3}$-alkyl, allyl, $R^aR^bR^cSi$, $CR^aR^bOR^c$, wherein two adjacent groups $R^2$ may be linked with each other to form a bridging group $SiR^aR^b$, $CR^aR^b$ or $CR^aOR^b$—$CR^cOR^b$; and
R' denotes hydrogen or $C_{1-6}$-alkyl;

$R^a$, $R^b$, $R^c$ independently of one another denote $C_{1-4}$-alkyl, phenyl or phenyl-$C_{1-3}$-alkyl, while the alkyl groups may be mono- or polysubstituted by halogen;

L1 independently of one another are selected from among fluorine, chlorine, bromine, $C_{1-3}$-alkyl, $C_{1-4}$-alkoxy and nitro;

while the phenyl groups mentioned in the definition of the above groups may be mono- or polysubstituted with L1;

comprising the steps (S2), (S3) and (S4):

(S2): reacting the organometallic compound of the formula VI

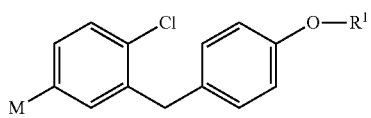

wherein $R^1$ is defined as hereinbefore and M denotes Li, Mg or MgQ, wherein Q denotes Cl, Br, I or an organic moiety; with a gluconolactone of general formula IV

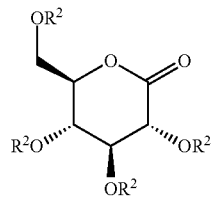

wherein $R^2$ is as hereinbefore defined, in an organic solvent or a mixture of two or more organic solvents; and (S3): adding an aqueous solution comprising one or more acids such that the reaction mixture forms an aqueous phase and an organic phase whereby the organic phase has a pH in the range from about 0 to 7; and (S4): separating the organic phase comprising the adduct obtained in the step (S2) from the aqueous phase; and (S5): reacting the obtained adduct with water or an alcohol R'—OH, where R' denotes $C_{1-6}$-alkyl, or a mixture thereof in the presence of one or more acids.

It was found that the separation of the aqueous and the organic phase in the step (S3) is more reliable and thus more suitable for a commercial scale process when the organic phase has a pH in the range from about 0 to 7. Thus in the step (S3) the aqueous solution comprising one or more acids is to be added to the reaction mixture such that the organic phase has a pH in the range from about 0 to 7. As a consequence of the improvement in the phase separation the whole process for preparing a glucopyranosyl-substituted benzyl-benzene derivative of general formula III proved to be a robust process with which the product is obtained in high yields and in a high purity at commercially viable scales. A further advantage is that the changes of solvents during the process are kept to a minimum and that the length of time for the whole process is minimized.

In the hereinbefore described variant E of the example XVIII of the WO 2006/120208 an aqueous quenching step with aqueous NH$_4$Cl solution (25 weight-%) was performed also. But in attempts to upscale this process it was observed that the separation of the aqueous and the organic phase may cause difficulties, for example by the formation of three phases. According to this example a pH of about 9 to 10 is measured in the organic phase which is outside the preferred pH range according to the step (S3) of the present invention.

In another aspect the present invention relates to a use of the process for preparing a glucopyranosyl-substituted benzyl-benzene derivative of general formula III,

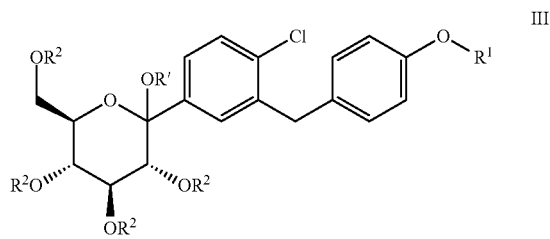

wherein $R^1$ denotes $C_{1-3}$-alkyl, cyclobutyl, cyclopentyl, cyclohexyl, R-tetrahydrofuran-3-yl, S-tetrahydrofuran-3-yl or tetrahydropyran-4-yl; and $R^2$ independently of one another denote hydrogen, ($C_{1-8}$-alkyl)carbonyl, ($C_{1-8}$-alkyl)oxycarbonyl, phenylcarbonyl, phenyl-($C_{1-3}$-alkyl)-carbonyl, phenyl-$C_{1-3}$-alkyl, allyl, $R^aR^bR^cSi$, $CR^aR^bOR^c$, wherein two adjacent groups $R^2$ may be linked with each other to form a bridging group $SiR^aR^b$, $CR^aR^b$ or $CR^aOR^b$—$CR^aOR^b$; and R' denotes hydrogen or $C_{1-6}$-alkyl;

$R^a$, $R^b$, $R^c$ independently of one another denote $C_{1-4}$-alkyl, phenyl or phenyl-$C_{1-3}$-alkyl, while the alkyl groups may be mono- or polysubstituted by halogen;

L1 independently of one another are selected from among fluorine, chlorine, bromine, $C_{1-3}$-alkyl, $C_{1-4}$-alkoxy and nitro;

while the phenyl groups mentioned in the definition of the above groups may be mono- or polysubstituted with L1;

as described hereinbefore and hereinafter for the synthesis of a glucopyranosyl-substituted benzyl-benzene derivative of general formula II,

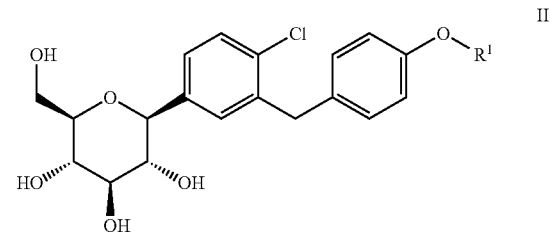

wherein $R^1$ is defined as hereinbefore comprising the step (S6):

(S6) reacting the glucopyranosyl-substituted benzyl-benzene derivative of general formula III with a reducing agent.

DETAILED DESCRIPTION OF THE INVENTION

Unless otherwise stated, the groups, residues and substituents, particularly $R^1$, $R^2$, R', $R^a$, $R^b$, $R^c$, L1, M, X, are defined as above and hereinafter.

If residues, substituents or groups occur several times in a compound, they may have the same or different meanings.

In the processes and compounds according to this invention the following meanings of groups and substituents are preferred:

$R^1$ preferably denotes R-tetrahydrofuran-3-yl or S-tetrahydrofuran-3-yl.

$R^a$, $R^b$, $R^c$ independently of one another preferably denote methyl, ethyl, n-propyl or i-propyl, tert.-butyl or phenyl; most preferably methyl.

$R^2$ preferably denotes hydrogen, methylcarbonyl, ethylcarbonyl or trimethylsilyl. Most preferably $R^2$ denotes trimethylsilyl.

R' preferably denotes hydrogen, methyl or ethyl, most preferably methyl.

The starting material of the formula VI may be obtained by methods known to the one skilled in the art. The process according to the invention preferably comprises the additional step (S1) in order to obtain the organometallic compound of the formula VI:

(S1): reacting a compound of the formula V

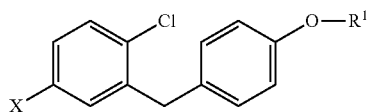

V wherein $R^1$ is defined as hereinbefore and X denotes Br, I or triflate;

with magnesium, lithium, a magnesium Grignard reagent or a lithium organic compound in an organic solvent or a mixture of two or more organic solvents yielding an organometallic compound of the formula VI

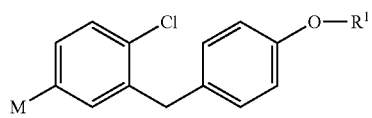

VI wherein $R^1$ is defined as hereinbefore and M denotes Li, Mg or MgQ, wherein Q denotes Cl, Br, I or an organic moiety;

In the following the processes according to this invention are described in detail.

The glucopyranosyl-substituted benzyl-benzene derivative of formula III may be synthesized from D-gluconolactone or a derivative thereof by reacting the desired benzyl-benzene compound in the form of an organometallic compound of the formula VI (Scheme 1).

Scheme 1: Addition of an Organometallic Compound to Gluconolactone

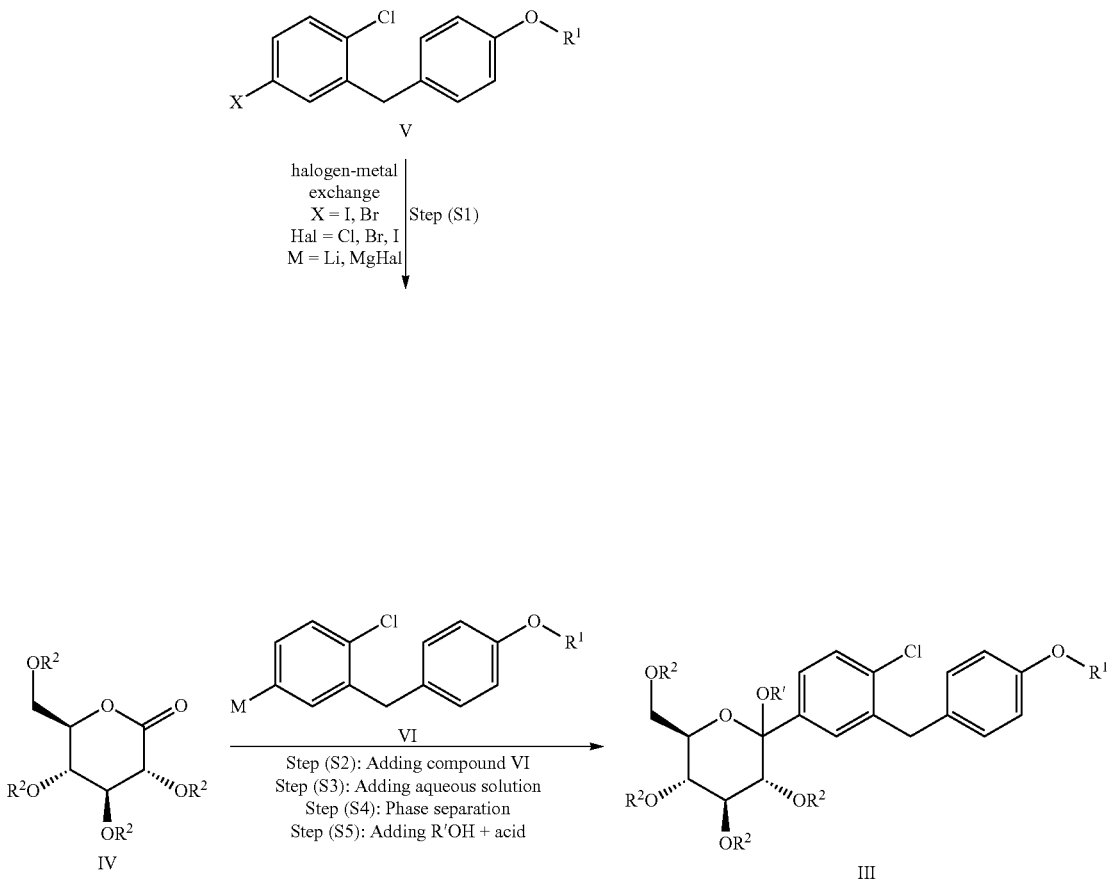

In the step (S1) the organometallic compound of the formula VI is prepared by reacting the compound of the formula V with magnesium, lithium, a magnesium Grignard reagent or a lithium organic compound in an organic solvent or a mixture of two or more organic solvents. The reaction is a so-called halogen-metal exchange reaction or an insertion of the metal into the carbon-halogen bond. The group X preferably denotes iodine. The reaction may be carried out with elemental magnesium or lithium. In case no spontaneous reaction takes place, promoters such as iodine, tetrachloromethane or iodomethane may be added. Alternatively the reaction may be carried out with a lithium organic compound, such as $C_{1-6}$-alkyl-lithium, preferably n-, sec- or tert-butyllithium. Preferably the reaction is carried out with a magnesium Grignard reagent, such as $C_{3-4}$-alkyl- or aryl-magnesium chlorides or bromides, for example as isopropyl or sec-butyl magnesium chloride or bromide, tert.-butyl magnesium chloride or bromide, phenyl magnesium chloride or bromide. The magnesium or lithium derivatized compounds thus obtained may optionally be transmetallated with metal salts such as e.g. cerium trichloride, zinc chloride or bromide, indium chloride or bromide, or copper bromide or chloride to form alternative organometal compounds (VI) suitable for addition. As promoters, additional salts such as lithium bromide and/or lithium chloride may be added at the beginning of, during or at the end of the step (S1). Alternatively such promoters may be added at the beginning or during the step (S2). Most preferably the compound of the formula V is reacted with a mixture of isopropylmagnesium chloride and lithium chloride. The molar ratio of the Grignard reagent, in particular of the $C_{3-4}$-alkyl-magnesium chloride or bromide, for example of iPrMgCl, to the lithium bromide and/or lithium chloride, in particular LiCl, is preferably in the range from 1:10 to 10:1, most preferably about 1:1. The 1:1 mixture of iPrMgCl:LiCl is commercially available, for example in a concentration of about 12 to 16% w/w in tetrahydrofuran, also called as "Turbogrignard-Solution". Preferred amounts of the magnesium, lithium, a magnesium Grignard reagent or a lithium organic compound relative to the compound of the formula V is in the range from about 0.5 to 2 mol, most preferably about equimolar. It was found that amounts smaller than about 1 mol lead to losses in yield and amounts greater than about 1 mol lead to the formation of unwanted by-products. The reaction is carried out in an organic solvent or a mixture of two or more organic solvents. Preferred solvents are selected from the group consisting of tetrahydrofuran, 2-methyltetrahydrofuran, tert.-butyl-methylether (TBME), diethylether, heptane, toluene, benzene, dioxane, methylcyclohexane, hexane, dimethyl sulfoxide, dichloromethane and chloroform. Most preferred solvents are tetrahydrofuran and 2-methyltetrahydrofuran. The reaction may be carried out in a temperature range from −100 to +50° C., preferably from −70 to 10° C., most preferably from −40 to −10° C. The reaction may be monitored by HPLC-, NIR-, IR-technology for example. A preferred reaction time is between 10 min and 600 min. The reaction product of the formula VI may be isolated, although such an isolation is not necessary. The foregoing reactions are preferably performed under inert gas atmosphere. Argon and nitrogen are preferred inert gases.

In the step (S2) the gluconolactone of the formula IV is added to the compound of the formula VI in an organic solvent or a mixture of two or more organic solvents. Preferred solvents are those described with regard to the previous step (S1). Preferably the gluconolactone is added to the reaction mixture obtained in the step (S1). The substituents $R^2$ preferably denote trimethylsilyl, triethylsilyl, triisopropyl, tributylsilyl, tert.-butyldimethylsilyl, tert.-butyldiphenylsilyl, acetyl, benzyl, benzoyl, allyl, methoxymethyl, tetrahydropyranyl. Most preferably $R^2$ denotes trimethylsilyl. Preferred amounts of the gluconolactone relative to the organometallic compound of the formula VI is in the range from about 0.8 to 3 mol, more preferably about 1 to 2 mol, most preferably about 1.06 mol. The reaction may be carried out in a temperature range from −100 to +50° C., preferably from −70 to 10° C., most preferably from −20 to −5° C. The reaction may be monitored by HPLC-, NMR, GC-, NIR- or IR-technology for example. A preferred reaction time is between 15 min and 600 min. The reaction product of the formula VI may be isolated. The foregoing reactions are preferably performed under inert gas atmosphere. Argon and nitrogen are preferred inert gases.

In the step (S3) an aqueous solution comprising one or more acids is added to the reaction mixture obtained in the step (S2) such that the reaction mixture forms an aqueous phase and an organic phase whereby the organic phase has a pH in the range from about 0 to 7. In principle all inorganic or organic acids may be used to obtain the desired pH range. Preferred acids are organic acids, such as citric acid, tartaric acid, oxalic acid, succinic acid, acetic acid, chloro acetic acid, dichloro acetic acid or trifluoroacetic acid, or inorganic acids, such as hydrochloric acid, sulphuric acid or nitric acid. The acid may be an ammonium salt, such as ammonium chloride. The acid may be part of a buffer system such as acetic acid/acetate (for example acetic acid and sodium acetate), dihydrogenphosphat/hydrogenphosphat (for example $KH_2PO_4/Na_2HPO_4$), TRIS (Tris(hydroxymethyl)-aminomethan) or HEPES (2-(4-(2-Hydroxyethyl)-1-piperazinyl)-ethanesulfonic acid). The more preferred acids are citric acid and acetic acid, in particular citric acid. The aqueous solution may additionally comprise mixtures of the aforementioned acids or additionally salts e.g. sodium chloride, potassium chloride, sodium bromide, potassium bromide, lithium chloride, lithium bromide or mixtures thereof. The amount of the one or more acids in the aqueous solution is preferably such that the reaction mixture forms an aqueous phase and an organic phase whereby the organic phase has a pH in the range from about 0 to 7. A more preferred pH range is from about 1 to 6, even more preferably from about 1 to 4, most preferably about 2 to 3. It was found that a pH in a preferred pH range as described above allows a good separation of the aqueous and the organic phase. Without being bound to any theory, it is assumed that at pH values in the preferred ranges the intermediate product has its highest stability. At pH values below the preferred ones the occurrence of three phases was observed. Again without being bound to any theory, it is thought that at low pH values protecting groups at the glucopyranosyl ring may be cleaved so that the deprotected intermediate product may form an additional phase. At pH values above the preferred ones phase separation was found to be difficult or impossible due to the formation of emulsions.

The pH value may be measured in the organic phase employing methods well known to the chemist such as pH electrodes and pH indicators, including indicator papers and test sticks. Preferably the pH value is measured at the given temperature of the organic phase, more preferably at a temperature between about 0° C. and 40° C., even more preferably between about 10° C. and 30° C., for example at room temperature (about 20 to 25° C.). The pH value may be measured in the organic phase after the phase separation, for example immediately after the separation or several hours later.

A preferred concentration of the one or more acids, such as for example citric acid, in the aqueous solution is in the range from about 2 to 30 weight-%, more preferably from about 5 to 20 weight-%, most preferably about 10 weight-%. The volume of the aqueous solution relative to the volume of the reaction mixture obtained in the step (S2) is preferably in the range from about 0.1 to 5, more preferably from about 0.2 to 2, even more preferably from about 0.2 to 1, most preferably about 0.3 to 0.6, for example about 0.4. The aqueous solution may be added to the reaction mixture preferably at a temperature in the range from about −50 to 40° C., even more preferably from about −10 to 25° C. The addition of the aqueous solution may be performed preferably within at least 15 min, even more preferably 60 min.

In order to achieve an even more improved separation of the aqueous and the organic phase it may be advantageous to add one or more additional organic solvents to the reaction mixture in this reaction step or during the previous reaction steps (S1) or (S2). Preferred additional organic solvents may be selected from the group consisting of 2-methyltetrahydrofurane, toluene, isopropyl acetate, ethyl acetate, n-butyl acetate, tert.-butylmethylether, n-heptane, acetone, methylethylketone, methylisobutylketone, dioxane, tetrahydrofuran, methylcyclohexane and hexane. The most preferred additional organic solvent is 2-methyltetrahydrofurane. The amount of the additional organic solvent relative to the total amount of the organic phase of the reaction mixture is preferably in the range from about 2 weight-% to 60 weight-%, more preferably from about 5 weight-% to 50 weight-%, even more preferably from about 10 weight-% to 40 weight-%, most preferably from about 15 to 35 weight-%.

Before the addition of the additional organic solvent the volume of the organic phase may be reduced by distillation of the reaction mixture, preferably under reduced pressure. The distillation is preferably performed at a temperature below or equal about 35° C. The reaction mixture obtained after the performance of the step (S3) exhibits an aqueous phase and an organic phase whereby the product of the reaction according to the step (S2) is found mainly in the organic phase.

In the step (S4) the organic phase comprising the adduct obtained in the step (S2) is separated from the aqueous phase. Methods for the separation of liquid phases are well known to the one skilled in the art. The separation of the phases is preferably performed at a temperature in the range from about −20 to 50° C., more preferably from about 0 to 30° C. The obtained organic phase comprises most of the adduct obtained in the step (S2). The aqueous phase may washed one or more times with an organic solvent or a mixture of organic solvents and the organic phases may be combined. Preferred organic solvents are described above with respect to the steps (S1), (S2) and (S3). Before performing the next reaction step a partial volume or the total volume of the one or more organic solvents is preferably distilled off, preferably under reduced pressure. The distillation is preferably performed at a temperature below or equal about 35° C.

In the step (S5) the adduct obtained in the step (S4) is reacted with water or an alcohol R'—OH, where R' denotes $C_{1-6}$-alkyl, or a mixture thereof in the presence of one or more acids. The alcohol R'—OH is preferably selected from the group consisting of methanol, ethanol, 1-propanol, 2-propanol, n-butanol, tert-butanol or mixtures thereof. The preferred alcohol is methanol. The alcohol is preferably employed in an amount exceeding an equimolar amount such that it serves as a solvent also. In principle all inorganic or organic acids may be used in the reaction step. With the addition of the one or more acids preferably a pH is to be obtained below about 7. A preferred pH range is from about 0 to 7, more preferably from about 0 to 4, even more preferably from about 1 to 2. The acid is preferably selected from the group consisting of hydrochloric acid, sulphuric acid, nitric acid, acetic acid, trifluoroacetic acid, citric acid, tartaric acid, oxalic acid and succinic acid. A more preferred acid is hydrochloric acid which may be employed for example as a solution of HCl in ethanol, HCl in propanol, HCl in dioxane. Alternatively HCl gas may be used. A preferred reaction temperature is in the range from about −50 to 50° C., more preferably from about 0 to 30° C., most preferably from about 15 to 25° C. A full conversion to the product of the formula III is advantageously achieved by a subsequent distillation, preferably at reduced pressure and preferably at a temperature below or equal about 35° C. It was found to improve the complete conversion when during the distillation a further amount of the alcohol R'—OH is added to the reaction mixture. The reaction is preferably completed within 120 min. The reaction may be monitored by HPLC for example. After the completion of the reaction the remaining acid in the reaction mixture is preferably partially or totally neutralized by the addition of one or more bases. A preferred pH after the addition of the base is preferably in the range from about 5 to 6. Preferred bases are for example triethylamine, ammonia, trimethylamine, n-alkylamines (such as e.g. methylamine, ethylamine), diisopropylethylamine (DIPEA), sodium carbonate, sodium bicarbonate, potassium carbonate, ethanolamine, 1,4-diazabicyclo[2.2.2]octan (DABCO), 1,8-diazabicyclo[5.4.0]undec-7-en (DBU). Triethylamine is the most preferred base. A partial or the total amount of the solvent is preferably distilled off, preferably at a reduced pressure. A solvent or a mixture of solvents is advantageously added and at least partially distilled off again. The addition of the solvent with subsequent distillation may be repeated one or more times in order to reduce the water content of the reaction mixture. The solvent is preferably selected from the group consisting of acetonitrile, propionitrile, tetrahydrofuran and dioxane. Finally another solvent or mixture of solvents may be added. A preferred solvent is selected from the group consisting of methylene chloride, ethyl acetate, isopropyl acetate, chloroform, 1,2-dichloroethane, dim ethoxyethane, dimethylformamide, N-methylpyrrolidon, dimethyl sulfoxide, tetrahydrofuran, 2-methyltetrahydrofuran, dioxane, diethylether and tert.-butylmethylether. A preferred solvent is dichloromethane. Advantageously the water content of the resulting reaction mixture is determined, for example via Karl-Fischer titration, GC, NMR, IR or NIR. The water content of the resulting reaction mixture is preferably below 5000 ppm, more preferably below 2000 ppm.

The glucose derivatives of formula II may be synthesized via the step (S6) which is a reduction of the anomeric carbon-oxygen bond of compound III (Scheme 2).

Scheme 2: Reduction of the compound III

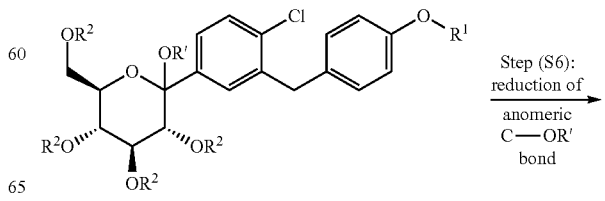

Step (S6): reduction of anomeric C—OR' bond

III

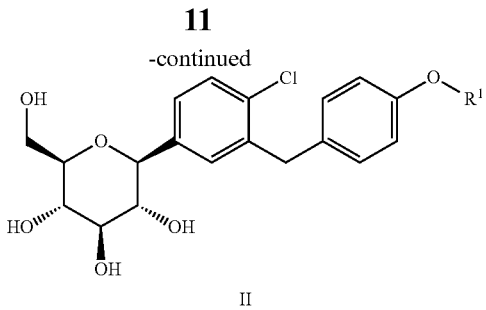

II

R', R¹ and R² are defined as hereinbefore. A preferred meaning of R² is hydrogen or tri-($C_{1-3}$-alkyl)silyl, such as trimethylsilyl. R' preferably denotes hydrogen or $C_{1-4}$-alkyl, in particular methyl or ethyl.

In the step (S6) the reduction may be conducted with one or more reducing agents in the presence of one or more Lewis acids or without a Lewis acid. Suitable reducing agents include for example silanes (such as e.g. triethylsilane, 1,1,3,3-tetramethyldisiloxane (TMDS), tripropylsilane, triisopropylsilane (TIPS), diphenylsilane), borane complexes (such as e.g. sodium cyanoborohydride ($NaCNBH_3$), zinc borohydride) or aluminium hydrides (such as e.g. lithium aluminium hydride ($LiAlH_4$), diisobutylaluminum hydride or lithium triisopropyl-aluminum hydride ($Li(iPr)_3AlH$)). A preferred reducing agent is triethylsilane. The amount of the reducing agent relative to the compound of the formula III is preferably in the range from about 1 to 5 mol, more preferably about 2 to 4 mol, most preferably about 2.7 mol. Suitable Lewis acids are for example aluminium chloride, boron trifluoride etherate, trimethylsilyl triflate, titanium tetrachloride, tin tetrachloride, scandium triflate, zinc iodide, or copper (II) triflate. Aluminium chloride is a preferred Lewis acid. The amount of the Lewis acid relative to the compound of the formula III is preferably in the range from about 1 to 5 mol, more preferably about 2 to 4 mol, most preferably about 2.1 mol. The reaction is performed in an organic solvent or a mixture of organic solvents. Preferred solvents are for example acetonitrile, dichloromethane, propionitrile, tetrahydrofuran or dioxane. Preferred solvents are acetonitrile, methylene chloride and mixtures thereof. Preferred reaction temperatures are between about −50° C. and 50° C., more preferably between about 0 and 30° C., most preferably between about 10 to 20° C. Preferably the reaction mixture obtained in the step (S4) is added to a mixture of the one or more Lewis acids, the one or more organic solvents and the one or more reducing agents. The addition of the reaction components is done preferably in a range from about 15 to 600 min, more preferably in a range between 45 and 120 min. The reaction mixture is preferably stirred, for example for about 0 to 600 min, more preferably for about 30 to 120 min at a temperature in the range from about −80 to 50° C., preferably about 0 to 35° C., most preferably about 15 to 25° C.

Alternatively, in the step (S6) hydrogen may be used as reducing agent. This reaction may be accomplished in the presence of a transition metal catalyst such as palladium on charcoal, Raney nickel, platinum oxide, palladium oxide. Suitable reaction conditions and solvents in a hydrogenation are known to the one skilled in the art. For example suitable solvents are tetrahydrofuran, ethyl acetate, methanol, ethanol, water, or acetic acid and suitable reaction temperatures are in the range from about −40° C. to 100° C. and suitable hydrogen pressures are in the range from about of 1 to 10 Torr.

The foregoing reduction synthesis steps are preferably performed under inert gas atmosphere. Argon and nitrogen are preferred inert gases.

After completion of the reaction water is added to the reaction mixture. During the addition the internal temperature is preferably in the range from 20 to 40° C. A preferred time range for the addition is preferably 15 to 120 min. Instead of water an aqueous solution may be added. Suitable aqueous solutions are for example salt solutions such as sodium chloride solution (brine), potassium chloride solution, $NaHCO_3$ solution, $Na_2CO_3$ solution or $K_2CO_3$ solution. Alternatively aqueous buffer solutions may be employed such as solutions of ammonium chloride, acetic acid/acetate, $KH_2PO_4/Na_2HPO_4$, TRIS (Tris(hydroxymethyl)-aminomethan), HEPES (2-(4-(2-Hydroxyethyl)-1-piperazinyl)-ethanesulfonic acid).

According to a preferred embodiment the reaction is partially distilled, either under reduced pressure or under atmospheric pressure and at a temperature below or equal about 35° C., more preferably below or equal about 55° C.

Then the reaction mixture is cooled to about 30 to 35° C. and the aqueous phase and the organic phase are separated. The aqueous phase may washed one or more times with an organic solvent or a mixture of organic solvents and the organic phases may be combined.

Advantageously an organic solvent or a mixture of organic solvents is added to the organic phase and part of or the total amount of the solvents is distilled off, preferably under reduced pressure and at a temperature below or equal about 35° C., more preferably below or equal about 40 to 50. Suitable solvents are toluene, isopropyl acetate. n-butyl acetate, ethyl acetate, tert.-butylmethylether, n-heptane, acetone, methylethylketone, methylisobutylketone, dioxane, tetrahydrofuran, benzene, methylcyclohexane, hexane, 2-methyltetrahydrofurane or mixtures thereof. Toluene is a preferred solvent.

The product may be obtained by crystallisation, for example as described in the WO 2006/117359, or as described hereinafter.

Alternatively in a further step before the crystallisation, an organic solvent or a mixture of organic solvents is added to the organic phase at a temperature below or equal about 40 to 50° C. Suitable solvents are acetonitrile, propionitrile, toluene, isopropyl acetate, n-butyl acetate, ethyl acetate, tert.-butylmethylether, n-heptane, acetone, methylethylketone, methylisobutylketone, dioxane, tetrahydrofuran, benzene, methylcyclohexane, hexane, 2-methyltetrahydrofurane or mixtures thereof. Acetonitrile is a preferred solvent.

Then the percentage of acetonitrile in the organic phase is determined with GC (gas chromatography) technology. The percentage of acetonitrile is in a range of about 10 to 40%, preferably between about 20 and 30%.

Then seeding crystals are added to the organic phase at a temperature range of about 40 to 48° C., preferably at about 45° C. Advantageously stirring is continued at this temperature range for about 10 to 240 min, more preferably 15 to 120 min.

Then the organic phase is cooled from a temperature range from about 40 to 48° C. to a temperature range of about 15 to 20° C. in a time range from 30 to 120 min, preferably about 60 min.

Then water or an aqueous solution is added to the organic phase. The addition of water or of the aqueous solution is preferably done in a temperature range of about 15 to 25° C., preferably 20° C. Furthermore the addition is preferably done a range of about 30 to 120 min, preferably about 60 min. Suitable aqueous solutions are for example salt solutions such as sodium chloride solution (brine), potassium chloride solution, NaHCO$_3$ solution, Na$_2$CO$_3$ solution or K$_2$CO$_3$ solution, or aqueous buffer solution. Aqueous buffer solutions are for example solutions of ammonium chloride, acetic acid/acetate, KH$_2$PO$_4$/Na$_2$HPO$_4$, TRIS (Tris(hydroxymethyl)-aminomethan), HEPES (2-(4-(2-Hydroxyethyl)-1-piperazinyl)-ethanesulfonic acid).

Then preferably the mixture is cooled to a temperature range of about 0 to 5° C. in a time range of about 45 to 120 min, preferably about 60 min. Then preferably the mixture is continued stirring for about 3 to 24 hrs, preferably about 12 hrs at a temperature range of about 0 to 5° C.

The product is then collected using suitable filtration or centrifugation techniques and the collected product is then washed with an organic solvent. Suitable solvents are acetonitrile, propionitrile, toluene, isopropyl acetate, n-butyl acetate, ethyl acetate, tert.-butylmethylether, n-heptane, acetone, methylethylketone, methylisobutylketone, dioxane, tetrahydrofuran, benzene, methylcyclohexane, hexane, 2-methyltetrahydrofurane or mixtures thereof. Preferred solvent is toluene.

Advantageously the isolated product is then dried using suitable drying equipment in a time range of about 1 to 192 hrs, preferably about 5 to 96 hrs at temperatures from about 20 to 120° C., preferably about 20 to 70° C. The drying is preferably performed under reduced pressure and under inert gas atmosphere. Argon and nitrogen are preferred inert gases.

The gluconolactone of the formula IV may be synthesized starting from D-(+)-gluconic acid-delta-lactone of the formula IVa (Scheme 3).

Scheme 3: Synthesis of the gluconolactone IV

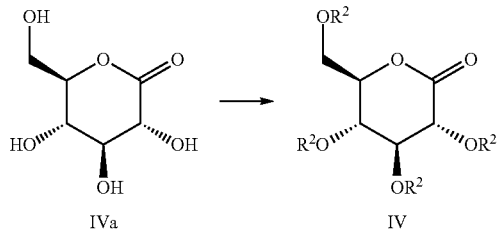

Methods for the transformation of the D-(+)-gluconic acid-delta-lactone of the formula IVa to yield the desired gluconolactone of the formula IV, wherein R$^2$ is defined as hereinbefore, are well known to the one skilled in the art. In the following a preferred method wherein R$^2$ denotes trimethylsilyl is described in detail.

A suspension of D-(+)-gluconic acid-delta-lactone of the formula IV in an organic solvent or mixture of organic solvents, one or more bases and one or more catalysts is treated with one or more silylating agents. Preferred organic solvents are tetrahydrofuran, 2-methyltetrahydrofuran, dioxane, or also tert.-butylmethylether (TBME), diethylether, heptane, toluene, benzene or mixtures thereof. Preferred bases are 4-methylmorpholine, diisopropylethylamine (DIPEA), triethylamine (TEA), NaHCO$_3$, K$_2$CO$_3$, Na$_2$CO$_3$, KOH, NaOH. Preferred catalysts are 4-dimethylaminopyridine, pyridine, triethylamine. Preferred silylating agents are chlorotrimethylsilane, hexamethyldisilazane, bis(trimethylsilyl)acetamide, trimethylsilyl-imidazole, trimethylsilyldimethyldiamine, N,N'-bistrimethylsilylurea or mixtures thereof. The base is preferably employed in a molar excess, more preferably in a range from about 4 to 10 mol, most preferably from about 5 to 8 mol relative to the starting compound of the formula IV. A preferred amount of the catalyst is in the range from about 0.001 to 0.5 mol, more preferably from about 0.01 to 0.2 mol relative to the starting compound of the formula IV. With regard to the silylating agent a preferred amount is in the range from about 4 to 10 mol relative to the starting compound of the formula IV. The reaction is preferably performed at a temperature in a range from about −50 to 100° C., more preferably from about −10 to 30° C. The addition of the silylating agent is preferably done in a time period from about 1 to 6 hours. After completion of the addition the reaction mixture is stirred, preferably within about 1 to 6 hours at a temperature from about −50 to 100° C., more preferably from about −10 to 30° C., in particular from 0 to 20° C. The conversion may be monitored with known methods, such as HPLC analysis, GC, NMR, IR. Then an organic solvent or mixture of organic solvents is added and the mixture is cooled, preferably to about 0 to 10° C. Preferred organic solvents are n-heptane, 2-methyltetrahydrofurane, dioxane, tert.-butylmethylether, diethylether, toluene, benzene, isopropylacetate, n-butyl acetate, ethylacetate. Then water or an aqueous solution is added, preferably at a temperature in the range from 0-10° C. The aqueous solution may comprise a salt such as sodium chloride solution, potassium chloride, NaHCO$_3$, Na$_2$CO$_3$, K$_2$CO$_3$, or a buffer system such as ammonium chloride, acetic acid, acetate, dihydrogenphosphat, hydrogenphosphat, TRIS (Tris(hydroxymethyl)-aminomethan), HEPES (2-(4-(2-Hydroxyethyl)-1-piperazinyl)-ethanesulfonic acid). After completion of the addition the mixture may be continued to be stirred, preferably at an internal temperature in a range from about −50 to 100° C., more preferably from about 0 to 35° C. After a discontinuation of the stirring the phases are separated and the organic layer is washed in succession one or more times with water or an aqueous solution as described hereinbefore. Then the organic solvent is distilled off, preferably at a temperature below or equal to about 40° C., in particular under reduced pressure. One or more organic solvents are added to the residue. Preferred organic solvents are n-heptane, methylcyclohexane, tert.-butylmethylether, 2-methyltetrahydrofurane, ethyl acetate, isopropyl acetate, n-butyl acetate, toluene, benzene. The resulting solution may be filtered. Then solvent is distilled off, preferably at a temperature below or equal to about 40° C., preferably under reduced pressure. The water content of the residue may be determined via Karl-Fischer analysis, GC, NMR or IR. The product is obtained as an oil.

The compound of the formula V may be synthesized starting from the ketone of the formula VII via a reduction (Scheme 4).

Scheme 4: Synthesis of the compound of the formula V

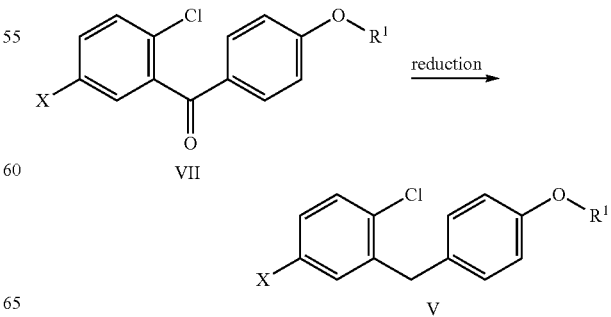

Methods for the reduction of a ketone of the formula VII to yield the desired compound of the formula V, wherein X is Br, I or triflate and $R^1$ is defined as hereinbefore, are well known to the one skilled in the art. In the following a preferred method wherein X denotes iodo is described in detail.

To a solution of the ketone of the formula VII and a Lewis acid in an organic solvent or a mixture of organic solvents a reducing agent is added. Suitable reducing agents are for example silanes such as 1,1,3,3-tetramethyldisiloxane, triethylsilane and triisopropylsilane, or borohydrides such as $NaBH_4$, or aluminum hydrides such as $LiAlH_4$. Preferred Lewis acids are aluminium chloride, $BF_3*OEt_2$, tris(pentafluorophenyl)borane, trifluoroacetic acid, hydrochloric acid, or $InCl_3$. Suitable organic solvents are for example halogenated hydrocarbons such as dichloromethane and 1,2-dichloroethane, toluene, benzene, hexane, acetonitrile and mixtures thereof, most preferably toluene. The reaction temperature is preferably in a range from about −30 to 80° C., preferably at 10 to 30° C., even more preferably from about 0 to 25° C. The amount of the reducing agent as well as the amount of the Lewis acid is preferably in the range from about 1 to 2 mol, more preferably about 1.2 mol relative to the ketone. The addition is performed preferably within about 1 to 5 hours, more preferably between about 1 to 2 hours. After completion of the addition, the mixture is stirred for preferably additional 1 to 2 hours. The conversion may be determined via HPLC analysis, GC, NMR or IR. Subsequently any excess of the reducing agent is preferably quenched by methods known to the one skilled in the art. For example the reaction mixture is treated with a ketone or an alcohol, such as acetone, methylethylketone, methanol, ethanol, 2-propanol or n-butanol, and stirred for about 1 to 5 hours, preferably at a temperature in the range from about 20 to 30° C. Any residual content of the reducing agent may be analyzed via GC, NMR or IR. It is advantageous to include a further reaction step wherein the reaction mixture is quenched with an aqueous solution. The aqueous solution (preferred pH range from 1 to 14) may comprise an acid such as hydrochloric acid, sulphuric acid, nitric acid, citric acid, tartaric acid, oxalic acid, succinic acid, acetic acid, trifluoroacetic acid, or a buffer system such as ammonium chloride, acetic acid/acetate, dihydrogenphosphate, hydrogenphosphate, TRIS (Tris(hydroxymethyl)-aminomethan), HEPES (2-(4-(2-Hydroxyethyl)-1-piperazinyl)-ethanesulfonic acid), or a base such as $NaHCO_3$, $K_2CO_3$, $Na_2CO_3$, KOH, NaOH. The reaction mixture is stirred, for example for about 30 to 120 min at an internal temperature of about 40 to 60° C. After completion the phases are separated and a partial or the total amount of the organic solvent is distilled off from the organic phase, preferably at a temperature below or equal to about 80° C., preferably under reduced pressure. The product of the formula V may be obtained via crystallisation. For this an organic solvent or a mixture of organic solvents is added to the residue, preferably at a temperature in the range from about 50 to 80° C. A mixture of toluene and ethanol is preferred, wherein a preferred weight ratio is from about 1:1 to 1:20, more preferably about 1:8. Toluene may be substituted by acetonitrile, tert.-butylmethylether, n-heptane, benzene, methylcyclohexane, 2-methyltetrahydrofurane, isopropyl acetate (IPAc), ethyl acetate (EtOAc) or n-butyl acetate. Ethanol may be substituted by 2-propanol, n-butanole, acetone, methylethylketone, water or tetrahydrofuran. The reaction mixture is cooled, preferably to a temperature in the range about 0 to 50° C., more preferably to about 20-40° C. Preferably seeding crystals are added which may be obtained for example according to WO 2006/117359. Stirring may be continued at this temperature, for example for 30 to 60 min. Then the mixture may be cooled further, for example to about −10° C. to 5° C. and stirred for an additional time. The product of the formula V may be collected, for example on a filter or on a centrifuge, and washed with a suitable solvent or mixture of solvents, such as ethanol. The product may be dried, preferably at a temperature below or equal to about 60° C., more preferably about 40° C., and under reduced pressure.

The ketone of the formula VII may be synthesized starting from the ketone of the formula VIII (Scheme 5).

Scheme 5: Synthesis of the ketone of the formula VII

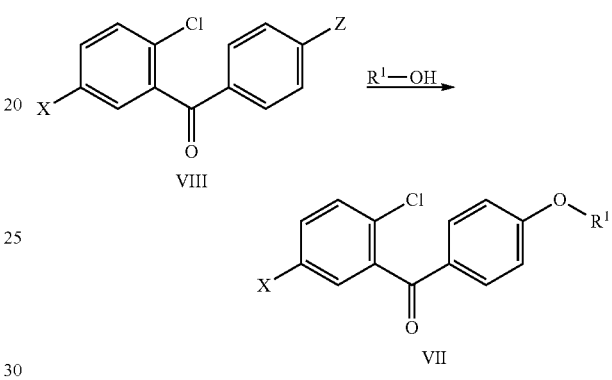

Methods for the replacement, in particular via nucleophilic substitution, of the group Z by the group $O—R^1$, wherein $R^1$ is defined as hereinbefore and Z preferably denotes fluorine, are well known to the one skilled in the art. The group X is defined as hereinbefore. In the following a preferred method is described in detail.

The ketone of the formula VIII is reacted with an alkanol $R^1$—OH, wherein $R^1$ is defined as hereinbefore, in an organic solvent or mixture of two or more organic solvents. The amount of the alkanol $R^1$—OH is preferably in the range of about 1 to 2 mol, more preferably 1.1 mol per mol of the ketone of the formula VIII. This reaction is preferably carried out in the presence of a base such as alkali $C_{1-4}$-alkoxides, alkali carbonates, alkali hydroxides, alkali phosphates, tri($C_{1-3}$ alkyl)amines and other N-containing organic bases. Examples of preferred bases are lithium or sodium or potassium tert-butanolate, sodium or potassium or cesium carbonate, sodium or potassium hydroxide, tripotassium phosphate, triethylamine, ethyldiisopropylamine, sodium bis(trimethylsilyl)amide (NaHMDS), diazabicycloundecene (DBU), 1,4-diazabicyclo[2.2.2]octane (DABCO) or mixtures thereof. More preferred bases are selected from sodium or potassium tert-butanolate, sodium or potassium hydroxide, cesium carbonate, a mixture of cesium carbonate and potassium carbonate, or mixtures thereof. The amount of the base is preferably in the range from 1 to 5 mol, more preferably about 1 to 2 mol, in particular about 1.2 mol base per mol of intermediate VIII. In case the base is a carbonate, phosphate or mixtures thereof, the total amount of the base is more preferably in the range from 2 to 4 mol base, most preferably about 3 mol base per mol of intermediate VIII. A more preferred base potassium-tert-butanolate, for example as an about 10 to 30% by weight solution in tetrahydrofuran. Suitable organic solvents are for example tetrahydrofuran, 2-methyltetrahydrofuran or dioxane. A preferred time period for the addition of the reactants is about 1 to 20 hours, preferably 2.5 to 6.5 hours. A preferred temperature during the addition of the reactants is in the range from about −20 to 70° C., more preferably about 15 to 25° C. After completion of the addition, the mixture is preferably stirred for a period of about 5 to 500 min at a temperature in the range from about −20 to 70° C., more preferably from about 15 to 25° C. The reaction may be monitored for example via HPLC analysis, NMR or IR. Then water or an aqueous solution is added. The aqueous solution may comprise an acid such as hydrochloric acid, sulphuric acid, nitric acid, citric acid, tartaric acid, oxalic acid, succinic acid, acetic acid, trifluoroacetic acid, or a buffer system such as ammonium chloride, acetic acid/acetate, dihydrogenphosphate, hydrogenphosphate, TRIS (Tris(hydroxymethyl)-aminomethan), HEPES (2-(4-(2-Hydroxyethyl)-1-piperazinyl)-ethanesulfonic acid), or a base such as $NaHCO_3$, $K_2CO_3$, $Na_2CO_3$, KOH, NaOH. The reaction mixture is stirred, for example for about 5 to 500 min at an internal temperature of about −20 to 70° C., more preferably from about 15-30° C.

After completion the phases are separated and a partial or the total amount of the organic solvent is distilled off from the organic phase, preferably at a temperature below or equal to about 50° C., preferably under reduced pressure. The product of the formula VII may be further purified and isolated. For this an organic solvent or a mixture of organic solvents is added to the residue, preferably at a temperature in the range from about 40 to 50° C. Preferred solvents are for example 2-propanol, methanol, ethanol, 1-propanol, n-butanol, acetone, methylethylketone, isopropyl acetate, ethyl acetate, n-butyl acetate, tert.-butylmethylether, n-heptane, methylcyclohexane, 2-methyltetrahydrofuran, acetonitrile, water, toluene, tetrahydrofuran, dioxane, methylene chloride, N-methylpyrrolidone, N,N'-dimethylformamide or mixtures thereof. The reaction mixture is cooled, preferably to a temperature in the range about −25 to 40° C., more preferably to about −5 to 5° C. The cooling may take place in a period of about 0.1 to 20 hours. The product of the formula VII may be collected, for example on a filter or on a centrifuge, and washed with a suitable solvent or mixture of solvents, such as 2-propanol and/or tert.-butylmethylether. Other suitable solvents were described hereinbefore. The product may be dried, preferably at a temperature below or equal to about 70° C., more preferably about 45° C., and under reduced pressure.

The ketone of the formula VIII may be synthesized starting from the benzoic acid derivative of the formula IX (Scheme 6).

Scheme 5: Synthesis of the keton of the formula VIII

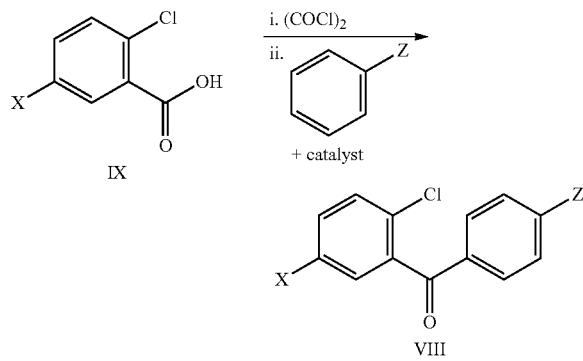

Starting from the benzoic acid derivative of the formula IX wherein X denotes Br, I or triflate, preferably iodine, the corresponding chloro-benzoic acid is advantageously obtained by reaction with oxalylchloride. This reaction is preferably performed in the presence of a catalyst, such as dimethylformamide. The reaction conditions and solvents are well known to the one skilled in the art. For example the fluorobenzene may be taken as a solvent in the first reaction step i.) which then forms the reactant (Z denotes fluorine) in the second reaction step ii.).

The second reaction step ii.) can be characterized as Friedel-Crafts or Friedel-Crafts-type acylation, a well-known method in organic synthesis. In principal, the chloro benzoic acid may be replaced by other benzoic acid derivatives such as e.g. benzoyl anhydrides, esters, or benzonitriles. This reaction is advantageously carried out in the presence of a catalyst such as $AlCl_3$, $FeCl_3$, iodine, iron, $ZnCl_2$, sulfuric acid, or trifluoromethanesulfonic acid, all of which are used in catalytic or up to stoichiometric amounts. A preferred catalyst is $AlCl_3$. The reaction may be performed with or without additional solvents. Additional solvents are chlorinated hydrocarbons such as e.g. dichloromethane or 1,2-dichloroethane, or hydrocarbons such as hexane or mixtures thereof. According to a preferred embodiment the reaction is carried out using an excess of the fluorobenzene which additionally serves as a solvent. Preferred temperatures during the reaction range from −30 to 140° C., preferably from 15 to 60° C. After completion of the reaction the reaction mixture may be quenched with water. Preferably the organic solvents are removed. The intermediate VIII may be isolated, preferably by crystallization, for example from water, $C_{1-3}$-alkanoles and mixtures thereof, such as water/2-propanole.

Moreover, the compounds and intermediates obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds and intermediates obtained which occur as racemates may be separated by methods known per se (cf. Allinger N. L. and Eliel E. L. in "Topics in Stereochemistry", Vol. 6, Wiley Interscience, 1971) into their optical antipodes and compounds or intermediates with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds and intermediates of the present invention may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds according to the invention are advantageously also obtainable using the methods described in the examples that follow, which may also be combined for this purpose with methods known to the skilled man from the literature, for example, particularly the methods described in WO 2006/120208, WO 2006/117359 and WO 2005/092877.

In the foregoing and following text, H atoms of hydroxyl groups are not explicitly shown in every case in structural formulae. The Examples that follow are intended to illustrate the present invention without restricting it. The terms "room temperature" or "ambient temperature" denote a temperature of about 20° C.

GC gas chromatography
hrs hours
i-Pr iso-propyl
Me methyl
min minutes
THF tetrahydrofuran
Experimental Procedures:

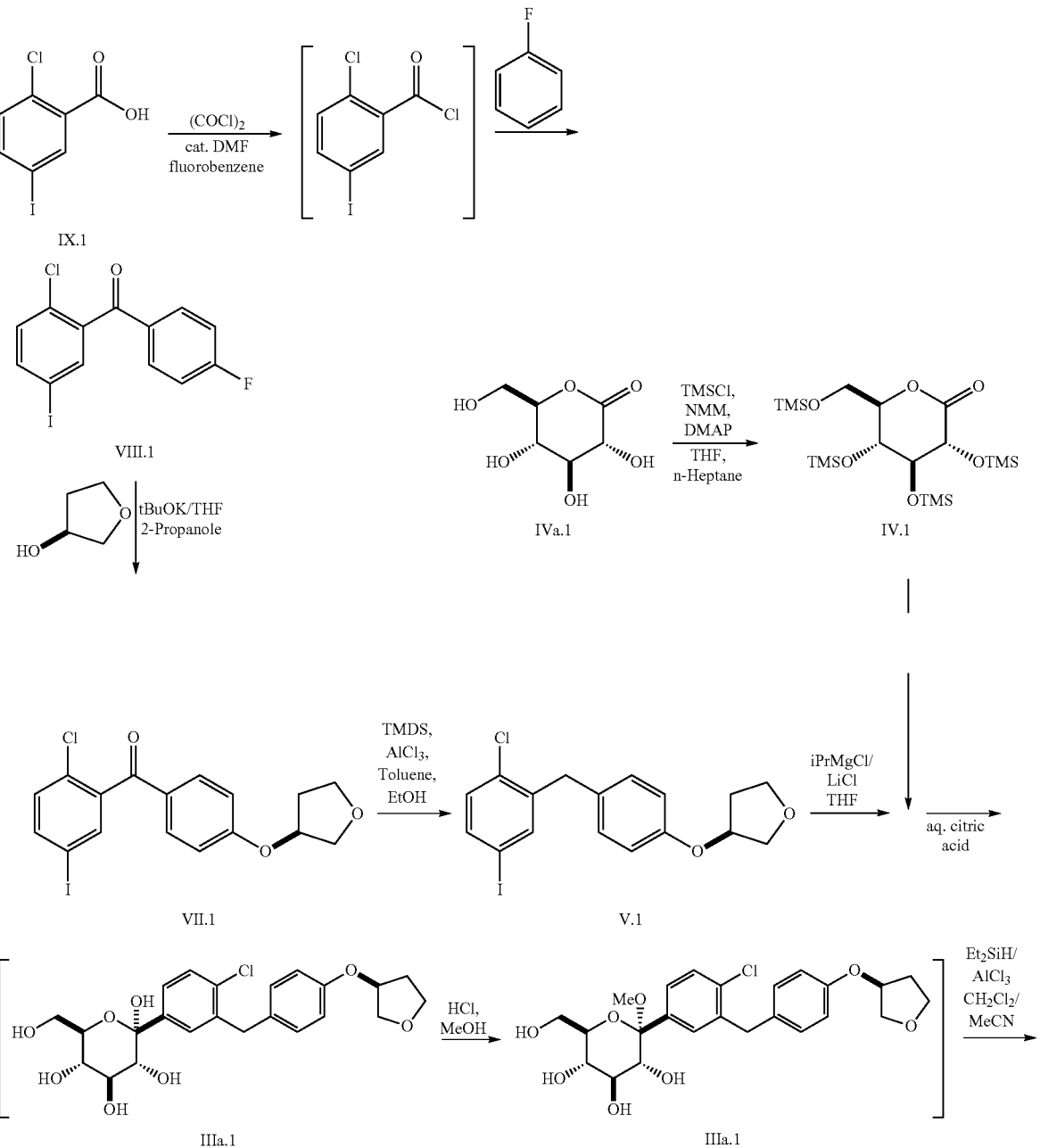

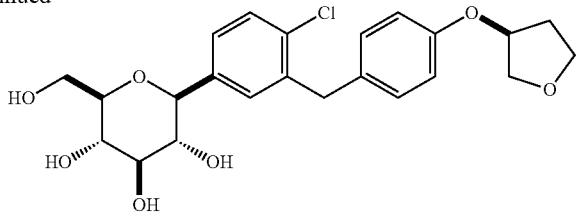

II.1

Example 1: Synthesis of the Fluoride VIII.1

Oxalylchloride (176 kg; 1386 mol; 1.14 eq) is added to a mixture of 2-chloro-5-iodo benzoic acid (343 kg; 1214 mol) (compound IX.1), fluorobenzene (858 kg) and N,N-dimethylformamide (2 kg) within 3 hours at a temperature in the range from about 25 to 30° C. (gas formation).

After completion of the addition, the reaction mixture is stirred for additional 2 hours at a temperature of about 25 to 30° C. The solvent (291 kg) is distilled off at a temperature between 40 and 45° C. (p=200 mbar). Then the reaction solution (911 kg) is added to aluminiumchloride $AlCl_3$ (181 kg) and fluorobenzene (192 kg) at a temperature between about 25 and 30° C. within 2 hours. The reaction solution is stirred at the same temperature for about an additional hour. Then the reaction mixture is added to an amount of 570 kg of water within about 2 hours at a temperature between about 20 and 30° C. and stirred for an additional hour. After phase separation the organic phase (1200 kg) is separated into two halves (600 kg each). From the first half of the organic phase solvent (172 kg) is distilled off at a temperature of about 40 to 50° C. (p=200 mbar). Then 2-propanole (640 kg) is added. The solution is heated to about 50° C. and then filtered through a charcoal cartouche (clear filtration). The cartouche may be exchanged during filtration and washed with a fluorobenzene/2-propanole mixture (1:4; 40 kg) after filtration. Solvent (721 kg) is distilled off at a temperature of about 40 to 50° C. and p=200 mbar. Then 2-propanole (240 kg) is added at a temperature in the range between about 40 to 50° C. If the content of fluorobenzene is greater than 1% as determined via GC, another 140 kg of solvent are distilled off and 2-propanole (140 kg) is added. Then the solution is cooled from about 50° C. to 40° C. within one hour and seeding crystals (50 g) are added. The solution is further cooled from about 40° C. to 20° C. within 2 hours. Water (450 kg) is added at about 20° C. within 1 hour and the suspension is stirred at about 20° C. for an additional hour before the suspension is filtered. The filter cake is washed with 2-propanole/water (1:1; 800 kg). The product is dried until a water level of <0.06% w/w is obtained. The second half of the organic phase is processed identically. A total of 410 kg (94% yield) of product which has a white to off-white crystalline appearance, is obtained. The identity of the product is determined via infrared spectrometry.

Example 2: Synthesis of the Ketone VII.1

To a solution of the fluoride VIII.1 (208 kg), tetrahydrofuran (407 kg) and (S)-3-hydroxytetrahydrofuran (56 kg) is added potassium-tert-butanolate solution (20%) in tetrahydrofuran (388 kg) within 3 hrs at 16 to 25° C. temperature. After completion of the addition, the mixture is stirred for 60 min at 20° C. temperature. Then the conversion is determined via HPLC analysis. Water (355 kg) is added within 20 min at a temperature of 21° C. (aqueous quench). The reaction mixture is stirred for 30 min (temperature: 20° C.). The stirrer is switched off and the mixture is left stand for 60 min (temperature: 20° C.). The phases are separated and solvent is distilled off from the organic phase at 19 to 45° C. temperature under reduced pressure. 2-Propanol (703 kg) is added to the residue at 40 to 46° C. temperature and solvent is distilled off at 41 to 50° C. temperature under reduced pressure. 2-Propanol (162 kg) is added to the residue at 47° C. temperature and solvent is distilled off at 40 to 47° C. temperature under reduced pressure. Then the mixture is cooled to 0° C. within 1 hr 55 min. The product is collected on a centrifuge, washed with a mixture of 2-propanol (158 kg) and subsequently with tert.-butylmethylether (88 kg) and dried at 19 to 43° C. under reduced pressure. 227 kg (91.8%) of product are obtained as colourless solid. The identity of the product is determined via infrared spectrometry.

Example 3: Synthesis of the Iodide V.1

To a solution of ketone VII.1 (217.4 kg) and aluminium chloride ($AlCl_3$; 81.5 kg) in toluene (366.8 kg) is added 1,1,3,3-tetramethyldisiloxane (TMDS, 82.5 kg) within 1 hr 30 min (temperature: 18-26° C.). After completion of the addition, the mixture is stirred for additional 1 hr at a temperature of 24° C. Then the conversion is determined via HPLC analysis. Subsequently the reaction mixture is treated with acetone (15.0 kg), stirred for 1 hr 5 min at 27° C. temperature and the residual TMDS content is analyzed via GC. Then a mixture of water (573 kg) and concentrated HCl (34 kg) is added to the reaction mixture at a temperature of 20 to 51° C. (aqueous quench). The reaction mixture is stirred for 30 min (temperature: 51° C.). The stirrer is switched off and the mixture is left stand for 20 min (temperature: 52° C.). The phases are separated and solvent is distilled off from the organic phase at 53-73° C. temperature under reduced pressure. Toluene (52.8 kg) and ethanol (435.7 kg) are added to the residue at 61 to 70° C. temperature. The reaction mixture is cooled to 36° C. temperature and seeding crystals (0.25 kg) are added. Stirring is continued at this temperature for 35 min. Then the mixture is cooled to 0 to 5° C. and stirred for additional 30 min. The product is collected on a centrifuge, washed with ethanol (157 kg) and dried at 15 to 37° C. under reduced pressure. 181 kg (82.6%) of product are obtained as colourless solid. The identity of the product is determined via the HPLC retention time.

Example 4: Synthesis of the Lactone IV.1

A suspension of the D-(+)-gluconic acid-delta-lactone IVa.1 (42.0 kg), tetrahydrofuran (277.2 kg), 4-methylmorpholine (NMM; 152.4 kg) and 4-dimethylaminopyridine (DMAP; 1.44 kg) is treated with chlorotrimethylsilane (TM-SCl; 130.8 kg) within 50 min at 13 to 19° C. After completion of the addition stirring is continued for 1 hr 30 min at 20 to 22° C. and the conversion is determined via HPLC analysis. Then n-heptane (216.4 kg) is added and the mixture is cooled to 5° C. Water (143 kg) is added at 3 to 5° C. within 15 min. After completion of the addition the mixture is heated to 15° C. and stirred for 15 min. The stirrer is switched off and the mixture is left stand for 15 min. Then the phases are separated and the organic layer is washed in succession two times with water (143 kg each). Then solvent is distilled off at 38° C. under reduced pressure and n-heptane (130 kg) is added to the residue. The resulting solution is filtered and the filter is rinsed with n-heptane (63 kg) (filter solution and product solution are combined). Then solvent is distilled off at 39 to 40° C. under reduced pressure. The water content of the residue is determined via Karl-Fischer analysis (result: 0.0%). 112.4 kg of the product is obtained as an oil (containing residual n-heptane, which explains the yield of >100%). The identity of the product is determined via infrared spectrometry.

Example 5a: Synthesis of the Glucoside II.1

To a solution of the iodide V.1 (267 kg) in tetrahydrofuran (429 kg) is added Turbogrignard solution (isopropylmagnesium chloride/lithium chloride solution, 14 weight-% iPrMgCl in THF, molar ratio LiCl:iPrMgCl=0.9-1.1 mol/mol) (472 kg) at −21 to −15° C. temperature within 1 hr 50 min. On completion of the addition the conversion is determined via HPLC analysis. The reaction is regarded as completed when the area of the peak corresponding to the iodide V.1 is smaller than 5.0% of the total area of both peaks, iodide V.1 and the corresponding desiodo compound of iodide V.1. If the reaction is not completed, additional Turbogrignard solution is added until the criterion is met. In this particular case the result is 3.45%. Then the lactone IV.1 (320 kg) is added at −25 to −18° C. temperature within 1 hr 25 min. The resulting mixture is stirred for further 1 hr 30 min at −13 to −18° C. On completion the conversion is determined via HPLC analysis (for information). On completion, a solution of citric acid in water (938 L; concentration: 10%-weight) is added to the reaction mixture of a volume of about 2500 L at −13 to 19° C. within 1 hr 25 min.

The solvent is partially distilled off from the reaction mixture (residual volume: 1816-1905 L) at 20 to 30° C. under reduced pressure and 2-methyltetrahydrofuran (532 kg) is added. Then the stirrer is switched off and the phases are separated at 29° C. After phase separation the pH value of the organic phase is measured with a pH electrode (Mettler Toledo MT HA 405 DPA SC) or alternatively with pH indicator paper (such as pH-Fix 0-14, Macherey and Nagel). The measured pH value is 2 to 3. Then solvent is distilled off from the organic phase at 30 to 33° C. under reduced pressure and methanol (1202 kg) is added followed by the addition of a solution of 1.25N HCl in methanol (75 kg) at 20° C. (pH=0). Full conversion to the acetale III.1 is achieved by subsequent distillation at 20 to 32° C. under reduced pressure and addition of methanol (409 kg).

Completion of the reaction is obtained when two criteria are fulfilled:
1) The ratio of the sum of the HPLC-area of the alpha-form+ beta-form of intermediate III.1 relative to the area of intermediate IIIa.1 is greater or equal to 96.0%: 4.0%.
2) The ratio of the HPLC-area of the alpha-form of intermediate III.1 to the beta-form of III.1 is greater or equal to 97.0% to 3.0%.

In this particular case both criteria are met. Triethylamin (14 kg) is added (pH=7.4) and solvent is distilled off under reduced pressure, acetonitrile (835 kg) is added and further distilled under reduced pressure. This procedure is repeated (addition of acetonitrile: 694 kg) and methylene chloride (640 kg) is added to the resulting mixture to yield a mixture of the acetale III.1 in acetonitrile and methylene chloride. The water content of the mixture is determined via Karl Fischer titration (result: 0.27%).

The reaction mixture is then added within 1 hr 40 min at 10 to 19° C. to a preformed mixture of $AlCl_3$ (176 kg), methylene chloride (474 kg), acetonitrile (340 kg), and triethylsilane (205 kg). The resulting mixture is stirred at 18 to 20° C. for 70 min. After completion of the reaction, water (1263 L) is added at 20 to 30° C. within 1 hr 30 min and the mixture is partially distilled at 30 to 53° C. under atmospheric pressure and the phases are separated. Toluene (698 kg) is added to the organic phase and solvent is distilled off under reduced pressure at 22 to 33° C. The product is then crystallized by addition of seeding crystals (0.5 kg) at 31° C. and water (267 kg) added after cooling to 20° C. The reaction mixture is cooled to 5° C. within 55 min and stirred at 3 to 5° C. for 12 hrs. Finally the product is collected on a centrifuge as colourless, crystalline solid, washed with toluene (348 kg) and dried at 22 to 58° C. 211 kg (73%) of product are obtained. The identity of the product is determined via the HPLC retention time.

Example 5b: Synthesis of the Glucoside II.1

To a solution of the iodide V.1 (30 g) in tetrahydrofuran (55 mL) is added Turbogrignard solution (isopropylmagnesium chloride/lithium chloride solution, 14 weight-% iPrMgCl in THF, molar ratio LiCl:iPrMgCl=0.9-1.1 mol/mol) (53 g) at −14 to −13° C. temperature within 35 min. On completion of the addition the conversion is determined via HPLC analysis. The reaction is regarded as completed when the area of the peak corresponding to the iodide V.1 is smaller than 5.0% of the total area of both peaks, iodide V.1 and the corresponding desiodo compound of iodide V.1. If the reaction is not completed, additional Turbogrignard solution is added until the criterion is met. In this particular case the result is 0.35%. Then the lactone IV.1 (36 g) is added at −15 to −6° C. temperature within 15 min. The resulting mixture is stirred for further 1 hr at −6 to −7° C. On completion, the conversion is determined via HPLC analysis (for information). On completion, a solution of citric acid in water (105 mL; concentration: 10%-weight) is added to the reaction mixture at −15 to 10° C. within 30 min. The solvent is partially distilled off from the reaction mixture (residual volume: 200 mL) at 20 to 35° C. under reduced pressure and 2-methyltetrahydrofuran (71 mL) is added. Then the mixture is stirred for 25 min at 30° C. Then the stirrer is switched off and the phases are separated at 30° C. After phase separation the pH value of the organic phase is measured with a pH electrode (Mettler Toledo MT HA 405 DPA SC) or alternatively with pH indicator paper (such as pH-Fix 0-14, Macherey and Nagel). The measured pH value is 3. Then solvent is distilled off from the organic phase at 35° C. under reduced pressure and methanol (126 mL) is added followed by the addition of a solution of 1.25N HCl in methanol (10.1 mL) at 25° C. (pH=1-2). Full conversion to the acetale III.1 is achieved by subsequent distillation at 35° C. under reduced pressure and addition of methanol (47 mL).

Completion of the reaction is obtained when two criteria are fulfilled:
1) The ratio of the sum of the HPLC-area of the alpha-form+ beta-form of intermediate III.1 relative to the area of intermediate IIIa.1 is greater or equal to 96.0%:4.0%. In this particular case the ratio is 99.6%:0.43%.
2) The ratio of the HPLC-area of the alpha-form of intermediate III.1 to the beta-form of III.1 is greater or equal to 97.0% to 3.0%. In this particular case the ratio is 98.7%: 1.3%. Triethylamin (2.1 mL) is added (pH=9) and solvent is distilled off at 35° C. under reduced pressure, acetonitrile (120 mL) is added and further distilled under reduced pressure at 30 to 35° C. This procedure is repeated (addition of acetonitrile: 102 mL) and methylene chloride (55 mL) is added to the resulting mixture to yield a mixture of the acetale III.1 in acetonitrile and methylene chloride. The water content of the mixture is determined via Karl Fischer titration (result: 0.04%).

The reaction mixture is then added within 1 hr 5 min at 20° C. to a preformed mixture of AlCl$_3$ (19.8 g), methylene chloride (49 mL), acetonitrile (51 mL), and triethylsilane (23 g). The resulting mixture is stirred at 20 to 30° C. for 60 min. After completion of the reaction, water (156 mL) is added at 20° C. within 25 min and the mixture is partially distilled at 55° C. under atmospheric pressure and the phases are separated at 33° C. The mixture is heated to 43° C. and toluene (90 mL) is added and solvent is distilled off under reduced pressure at 41 to 43° C. Then acetonitrile (10 mL) is added at 41° C. and the percentage of acetonitrile is determined via GC measurement. In this particular case, the acetonitrile percentage is 27%-weight. The product is then crystallized by addition of seeding crystals (0.1 g) at 44° C. and the mixture is further stirred at 44° C. for 15 min. The mixture is then cooled to 20° C. within 60 min and water (142 mL) is added at 20° C. within 30 min. The reaction mixture is cooled to 0 to 5° C. within 60 min and stirred at 3° C. for 16 hrs. Finally the product is collected on a filter as colourless, crystalline solid, washed with toluene (80 mL) and dried at 20 to 70° C. 20.4 g (62.6%) of product are obtained. The identity of the product is determined via the HPLC retention time.

The invention claimed is:
1. Process for preparing a glucopyranosyl-substituted benzyl-benzene derivative of general formula III,

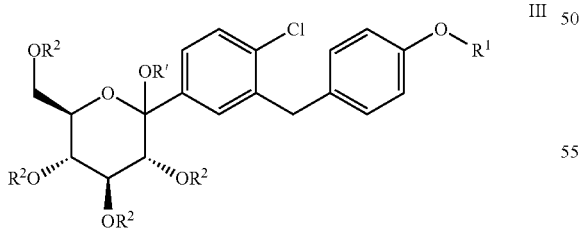

wherein
R$^1$ denotes (R)-tetrahydrofuran-3-yl or (S)-tetrahydrofuran-3-yl; and
R$^2$ denotes trimethylsilyl; and
R' denotes hydrogen or C$_{1-6}$-alkyl;
comprising the steps (S2), (S3) and (S4):
(S2): reacting the organometallic compound of the formula VI

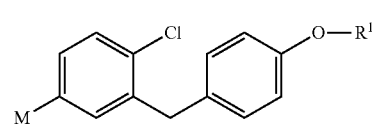

wherein R$^1$ is defined as hereinbefore and M denotes Li, Mg or MgQ, wherein Q denotes Cl, Br, I or an organic moiety;
with a gluconolactone of general formula IV

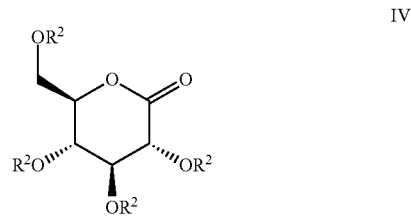

wherein R$^2$ is as hereinbefore defined,
in an organic solvent or a mixture of two or more organic solvents; and
(S3): adding an aqueous solution comprising tartaric acid such that the reaction mixture forms an aqueous phase and an organic phase whereby the organic phase has a pH in the range from about 1 to 4; and
(S4): separating the organic phase comprising the adduct obtained in the step (S2) from the aqueous phase; and
(S5): reacting the obtained adduct with water or an alcohol R'—OH, where R' denotes C$_{1-6}$-alkyl, or a mixture thereof in the presence of one or more acids.
2. The process according to the claim 1 additionally comprising the step (S1):
(S1): reacting a compound of the formula V

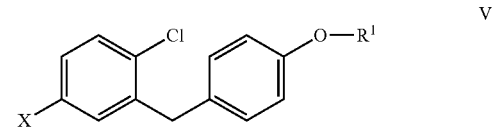

wherein R$^1$ is defined as in claim 1 and X denotes Br, I or triflate;
with magnesium, lithium, a magnesium Grignard reagent or a lithium organic compound in an organic solvent or a mixture of two or more organic solvents yielding an organometallic compound of the formula VI

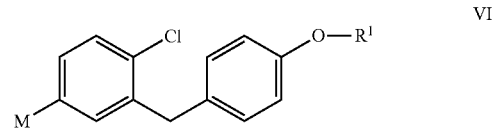

wherein R$^1$ is defined as hereinbefore and M denotes Li, Mg or MgQ, wherein Q denotes Cl, Br, I or an organic moiety.
3. The process according to the claim 2 wherein in the step (S1) the compound of the formula V is reacted with a C$_{3-4}$-alkyl-magnesium chloride or bromide.

4. The process according to the claim 3 wherein at the beginning of, during or at the end of the step (S1) and/or at the beginning or during the step (S2) lithium bromide and/or lithium chloride is added to the reaction mixture whereby the molar ratio of the $C_{3-4}$-alkyl-magnesium chloride or bromide to the lithium bromide and/or lithium chloride is in the range from 1:10 to 10:1.

5. The process according to claim 1 wherein the aqueous solution comprises 2 to 30 weight-% of tartaric acid.

6. The process according to claim 1 wherein the organic phase of the reaction mixture in the step (S3) comprises 2-methyltetrahydrofurane in an amount in the range from about 2 to 60 weight-% relative to the total amount of the organic phase of the reaction mixture.

7. The process according to claim 1
additionally comprising the step (S6):
(S6) reacting the glucopyranosyl-substituted benzyl-benzene derivative of general formula III with a reducing agent.

8. The process according to claim 1, wherein the solvent is selected from the group consisting of tetrahydrofuran, 2-methyltetrahydrofuran, tert.-butyl-methylether, diethylether, heptane, toluene, benzene, dioxane, methylcyclohexane, hexane, dimethyl sulfoxide, dichloromethane and chloroform.

9. The process according to claim 1, wherein the amount of the gluconolactone relative to the organometallic compound of the formula VI is in the range from about 0.8 to 3 mol.

10. The process according to claim 1, wherein R' denotes hydrogen, methyl or ethyl.

11. The process according to claim 1, wherein in the step (S5) the obtained adduct is reacted with an alcohol R'—OH, wherein the alcohol R'—OH is selected from the group consisting of methanol, ethanol, 1-propanol, 2-propanol, n-butanol, tert-butanol or mixtures thereof.

12. The process according to claim 1, wherein in the step (S5) with the addition of the one or more acids a pH is to be obtained in a pH range from about 0 to 7.

13. The process according to claim 1, wherein in the step (S5) the one or more acids are selected from the group consisting of hydrochloric acid, sulphuric acid, nitric acid, acetic acid, trifluoroacetic acid, citric acid, tartaric acid, oxalic acid and succinic acid.

14. The process according to claim 1, wherein in the step (S5) the reaction temperature is in the range from about −50 to 50° C.

15. The process according to claim 2, wherein the amount of the magnesium, lithium, a magnesium Grignard reagent or a lithium organic compound relative to the compound of the formula V is in the range from about 0.5 to 2 mol.

16. The process according to claim 2, wherein the reaction in step (S1) and/or step (S2) is carried out in a temperature range from −70 to 10° C.

17. The process according to claim 5, wherein the aqueous solution comprises 5 to 20 weight % of tartaric acid.

18. The process according to claim 6, wherein the amount of 2-methyltetrahydrofurane is in the range from about 10 to 40 weight-% relative to the total amount of the organic phase of the reaction mixture.

19. The process according to claim 1, wherein the organic phase in step (S3) has a pH in the range from about 2 to 3.

* * * * *